US012650262B2

(12) United States Patent
Womack et al.

(10) Patent No.: US 12,650,262 B2
(45) Date of Patent: Jun. 9, 2026

(54) FOOD WASTE DEHYDRATOR APPARATUS AND METHODS OF USE

(71) Applicant: Jason Womack, Kennesaw, GA (US)

(72) Inventors: Jason Womack, Marietta, GA (US); Bruce Works, Atlanta, GA (US)

(73) Assignee: Jason Womack, Kennesaw, GA (US)

( * ) Notice: Subject to any disclaimer, the term of this patent is extended or adjusted under 35 U.S.C. 154(b) by 638 days.

(21) Appl. No.: 18/120,946

(22) Filed: Mar. 13, 2023

(65) Prior Publication Data

US 2023/0288141 A1     Sep. 14, 2023

Related U.S. Application Data

(60) Provisional application No. 63/319,365, filed on Mar. 13, 2022.

(51) Int. Cl.
*F26B 11/16*          (2006.01)
*A23N 17/00*         (2006.01)
(Continued)

(52) U.S. Cl.
CPC .............. *F26B 11/16* (2013.01); *A61L 11/00* (2013.01); *B01F 27/1123* (2022.01); *B01F 27/1125* (2022.01); *B01F 27/191* (2022.01); *B01F 27/906* (2022.01); *B09B 3/40* (2022.01); *F26B 3/20* (2013.01); *F26B 3/347* (2013.01);
(Continued)

(58) Field of Classification Search
CPC .. F26B 11/16; F26B 3/20; F26B 3/347; F26B 7/00; F26B 21/35; F26B 25/12; F26B 3/24; F26B 11/14; F26B 21/25; F26B 21/333; F26B 25/04; F26B 2200/02; A61L 11/00; A61L 2/10; B01F 27/1123; B01F 27/1125; B01F 27/191; B01F 27/906; B09B 3/40; B09B 2101/70; B09B 3/00; A23N 17/004
See application file for complete search history.

(56) References Cited

U.S. PATENT DOCUMENTS 3,744,145 A     7/1973   Maxwell et al.
5,424,033 A  *  6/1995   Roland ..................... A61L 2/06
                                                              422/26
(Continued)

FOREIGN PATENT DOCUMENTS

JP        10538488 A     2/1993
KR    20050079981 A     8/2005
(Continued)

*Primary Examiner* — David J Laux
(74) *Attorney, Agent, or Firm* — GrowIP Law Group LLC

(57)          ABSTRACT

The disclosure provides an example food dehydrator apparatus for treating food waste and methods for use thereof. The apparatus includes: (a) a receptacle having a bottom support, a top support, and a cylindrical sidewall extending therebetween, where the receptacle has an interior cavity, where the top support has a first opening configured to receive the food waste, and where the bottom support has a first opening to release dehydrated food waste, (b) a load door, (c) a shaft rotatably arranged within the receptacle, (d) a gear motor coupled to the shaft, (e) a first plurality of paddles, (f) a second plurality of paddles, where the first and second plurality of paddles are static, (g) a third plurality of paddles, (h) a fourth plurality of paddles, (i) at least one heat source, and (j) a gate coupled to the bottom support of the receptacle.

42 Claims, 23 Drawing Sheets

(51) Int. Cl.

| | | |
|---|---|---|
| *A61L 11/00* | (2006.01) |
| *B01F 27/1123* | (2022.01) |
| *B01F 27/1125* | (2022.01) |
| *B01F 27/191* | (2022.01) |
| *B01F 27/906* | (2022.01) |
| *B09B 3/40* | (2022.01) |
| *B09B 101/70* | (2022.01) |
| *F26B 3/20* | (2006.01) |
| *F26B 3/347* | (2006.01) |
| *F26B 7/00* | (2006.01) |
| *F26B 21/35* | (2026.01) |
| *F26B 25/12* | (2006.01) |

(52) U.S. Cl.
CPC ............... *F26B 7/00* (2013.01); *F26B 21/35* (2026.01); *F26B 25/12* (2013.01); *A23N 17/004* (2013.01); *B09B 2101/70* (2022.01)

(56) References Cited

U.S. PATENT DOCUMENTS

| | | | |
|---|---|---|---|
| 6,502,980 B1 * | 1/2003 | Ekstrom ................. | B01F 27/50 |
| | | | 366/307 |
| 7,762,713 B2 | 7/2010 | Koh | |
| 7,883,040 B2 | 2/2011 | Lee et al. | |
| 7,966,744 B2 | 6/2011 | Kim et al. | |
| 8,043,558 B2 | 10/2011 | Chambe et al. | |
| RE44,676 E | 12/2013 | Lee | |
| 9,615,604 B2 | 4/2017 | Russick et al. | |
| 10,196,802 B2 | 2/2019 | Park et al. | |
| 2008/0184918 A1 | 8/2008 | Kim et al. | |
| 2010/0132210 A1 * | 6/2010 | Kruger ............... | B01F 27/1142 |
| | | | 34/259 |
| 2012/0039757 A1 | 2/2012 | Yoo et al. | |
| 2013/0042493 A1 | 2/2013 | Lee | |
| 2014/0027445 A1 * | 1/2014 | Scheurs ................... | H05B 6/76 |
| | | | 219/679 |
| 2015/0276312 A1 * | 10/2015 | Mardikian ................ | F26B 7/00 |
| | | | 34/61 |
| 2020/0001256 A1 * | 1/2020 | Chece ................. | B01F 27/0726 |
| 2020/0061561 A1 * | 2/2020 | Villarino, Jr. ........... | F16C 27/02 |
| 2020/0353474 A1 * | 11/2020 | Crepeau ............ | B01D 46/4227 |
| 2021/0113979 A1 * | 4/2021 | Schoen ................... | C05C 3/005 |

FOREIGN PATENT DOCUMENTS

| | | |
|---|---|---|
| KR | 100523363 B1 | 10/2005 |
| KR | 100646165 B1 | 11/2006 |
| KR | 20060116598 A | 11/2006 |
| KR | 100653205 B1 | 12/2006 |
| KR | 100827923 B1 | 5/2008 |
| KR | 20080057735 A | 6/2008 |
| KR | 20100029961 A | 3/2010 |
| KR | 20100041897 A | 4/2010 |
| KR | 20100091514 A | 8/2010 |
| KR | 20110076013 A | 7/2011 |
| KR | 101147225 B1 | 5/2012 |
| KR | 101409347 B1 | 6/2014 |
| KR | 20150096284 A | 8/2015 |

* cited by examiner

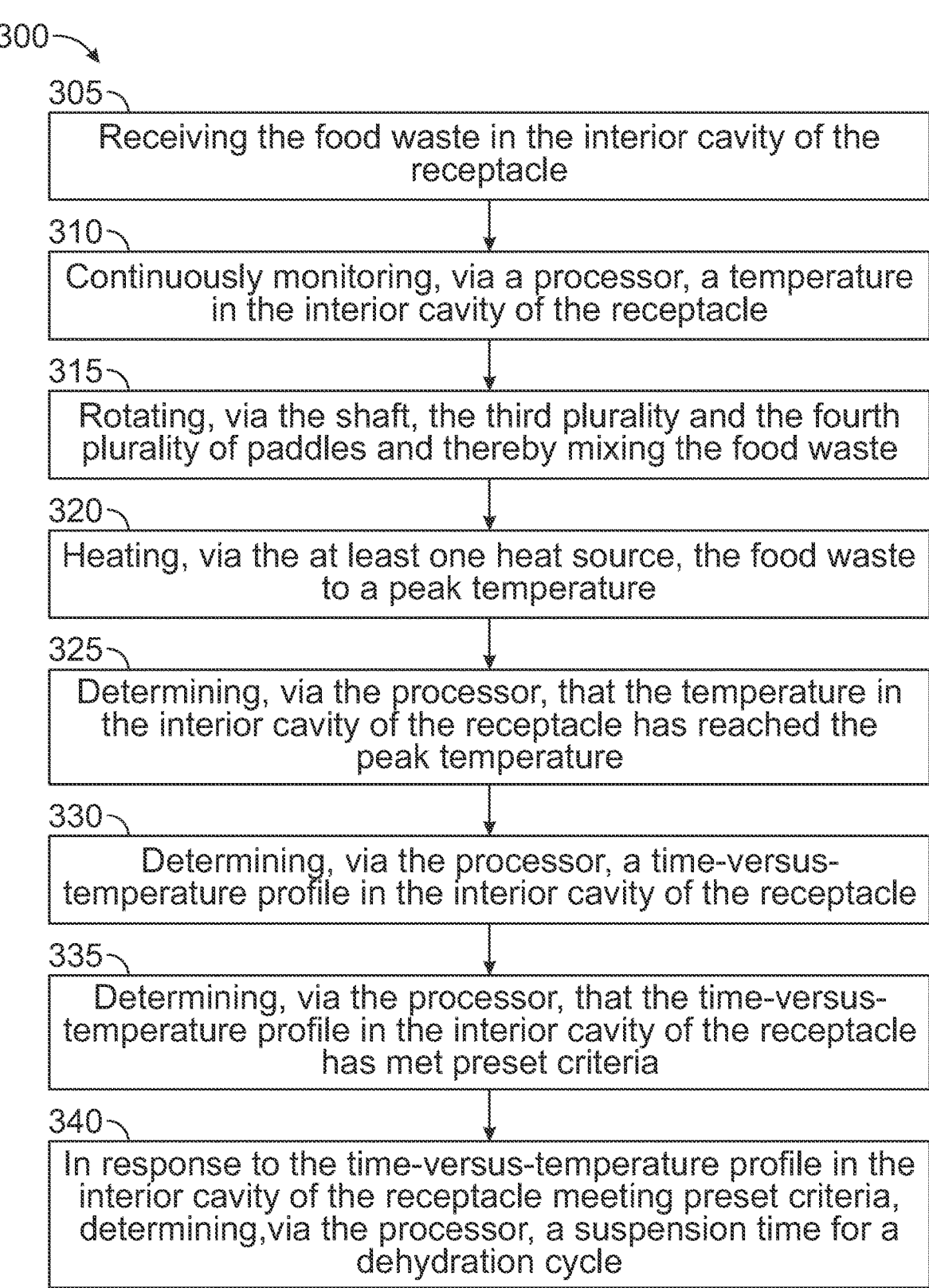

300

305
Receiving the food waste in the interior cavity of the receptacle

310
Continuously monitoring, via a processor, a temperature in the interior cavity of the receptacle 315
Rotating, via the shaft, the third plurality and the fourth plurality of paddles and thereby mixing the food waste 320
Heating, via the at least one heat source, the food waste to a peak temperature 325
Determining, via the processor, that the temperature in the interior cavity of the receptacle has reached the peak temperature 330
Determining, via the processor, a time-versus-temperature profile in the interior cavity of the receptacle 335
Determining, via the processor, that the time-versus-temperature profile in the interior cavity of the receptacle has met preset criteria 340
In response to the time-versus-temperature profile in the interior cavity of the receptacle meeting preset criteria, determining, via the processor, a suspension time for a dehydration cycle

FIG. 24

FOOD WASTE DEHYDRATOR APPARATUS AND METHODS OF USE

CROSS-REFERENCE TO RELATED APPLICATION

This application is a U.S. Non-Provisional application that claims priority to U.S. Provisional Patent Application No. 63/319,365, filed Mar. 13, 2022, which is hereby incorporated by reference in its entirety.

BACKGROUND

Food waste dehydrators remove water from food waste thereby creating material for composting or animal feed. Known food waste dehydrators utilize a barrel arranged on its side such that a cylindrical sidewall is arranged horizontally and have a central shaft extending between the ends of the barrel that is parallel to the ground. The corresponding device footprint of known food waste dehydrators is typically on the order of 36 inches×48 inches.

Known food waste dehydrators utilize air-cooled heat exchangers to cool air heated during the dehydration process with conditioned air from the occupied space. These air-cooled heat exchangers create a heat load on the occupied space requiring greater expense to cool the space.

SUMMARY

In a first aspect, an example apparatus for treating food waste is disclosed. The apparatus for treating food waste includes (a) a receptacle having a bottom support, a top support, and a cylindrical sidewall extending therebetween, where the receptacle has an interior cavity, where the top support has a first opening configured to receive the food waste, and where the bottom support has a first opening to release dehydrated food waste, (b) a load door coupled to the first opening in the top support, (c) a shaft rotatably arranged concentrically within the interior cavity of the receptacle and extending through a second opening in the bottom support of the receptacle and through a second opening in the top support of the receptacle such that the shaft is oriented vertically, (d) a gear motor coupled to the shaft via one or more gears, a roller chain, or a drive belt, (e) a first plurality of paddles each having a first end coupled to a first hub that is disposed concentrically about the shaft in a spaced-apart arrangement, the first plurality of static paddles each having a second end extending radially from the first hub such that the second end is coupled to the cylindrical sidewall of the receptacle, (f) a second plurality of paddles each having a first end coupled to a second hub that is disposed concentrically about the shaft in a spaced-apart arrangement below the first hub, the second plurality of static paddles each having a second end extending radially from the second hub such that the second end is coupled to the cylindrical sidewall of the receptacle, where the first and the second plurality of paddles are configured to be static, (g) a third plurality of paddles coupled to a third hub that is coupled to the shaft between the first hub and the second hub, (h) a fourth plurality of paddles coupled to a fourth hub that is coupled to the shaft between the second hub and the bottom surface of the receptacle, where the third plurality of paddles and the fourth plurality of paddles are configured to rotate with the shaft, (i) at least one heat source comprising one or more of (i) at least one heating pad coupled to the bottom support and/or the cylindrical sidewall of the receptacle, (ii) a heat exchanger coupled to the receptacle via an inlet opening and an outlet opening, and (iii) at least one microwave coupled to the top support and configured to emit microwaves into the interior cavity of the receptacle, and (j) a gate coupled to the bottom support of the receptacle, where the gate is configured to move between a closed position such that the gate creates a watertight seal with the first opening in the bottom support of the receptacle and an open position that permits the dehydrated food waste to exit the interior cavity of the receptacle through the first opening in the bottom support.

In a second aspect, an example method for operating the apparatus according to the first aspect is disclosed. The method includes (a) receiving the food waste in the interior cavity of the receptacle, (b) continuously monitoring, via a processor, a temperature in the interior cavity of the receptacle, (c) rotating, via the shaft, the third plurality and the fourth plurality of paddles and thereby mixing the food waste, (d) heating, via the at least one heat source, the food waste to a peak temperature; (e) determining, via the processor, that the temperature in the interior cavity of the receptacle has reached the peak temperature, (f) determining, via the processor, a time-versus-temperature profile in the interior cavity of the receptacle, (g) determining, via the processor, that the time-versus-temperature profile in the interior cavity of the receptacle has met preset criteria, and (h) in response to the time-versus-temperature profile in the interior cavity of the receptacle meeting preset criteria, determining, via the processor, a suspension time for a dehydration cycle.

The features, functions, and advantages that have been discussed can be achieved independently in various examples or may be combined in yet other examples further details of which can be seen with reference to the following description and drawings.

BRIEF DESCRIPTION OF THE FIGURES

FIG. 24 shows a flowchart of a method, according to an example implementation.

Figure 1:
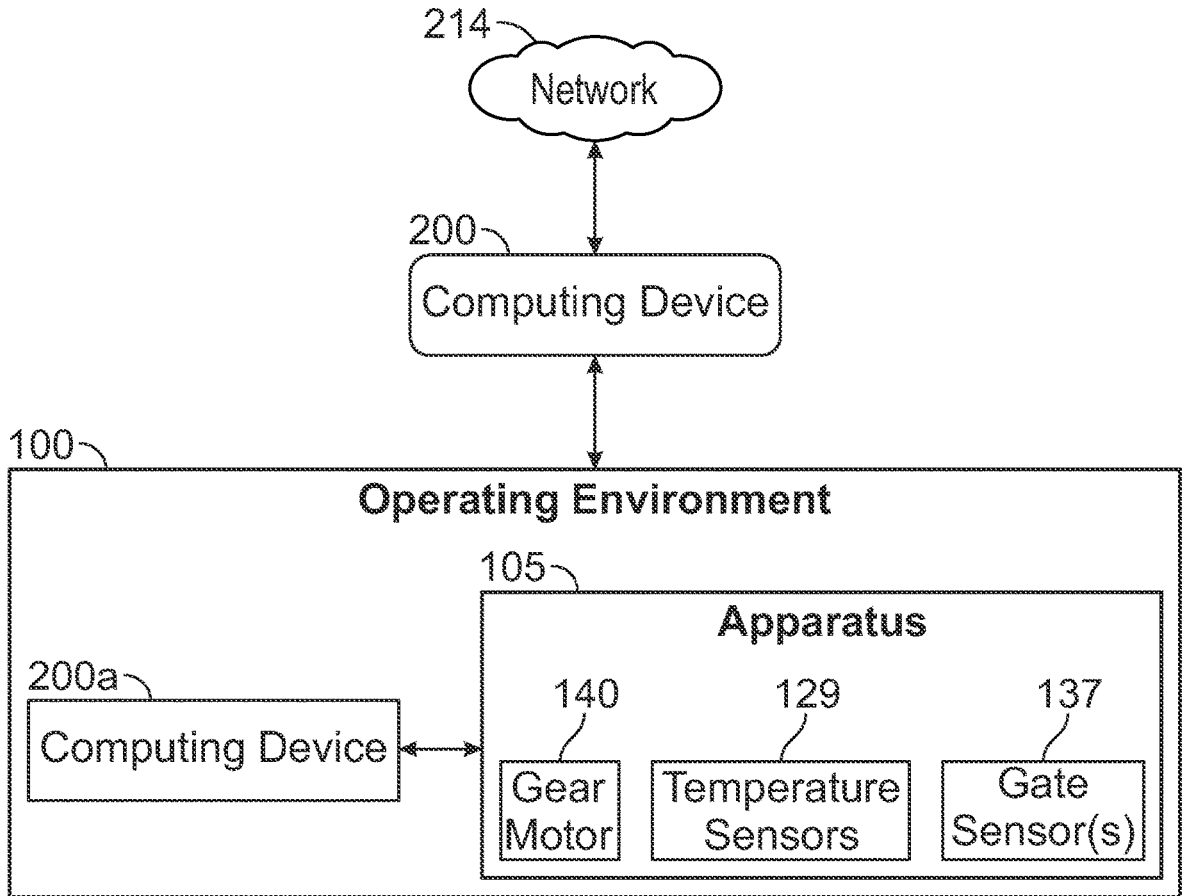
FIG. 1 is a functional block diagram of a system, according to one example implementation.

The drawings are for the purpose of illustrating examples, but it is understood that the disclosure is not limited to the arrangements and instrumentalities shown in the drawings.

DETAILED DESCRIPTION

Overview

Embodiments of the apparatus for treating food waste and methods of use thereof described herein can be used to reduce the footprint of the food dehydrator apparatus, reduce odors associated with food waste, reduce viruses and bacteria present in the food waste, and avoid or reduce a heat load imposed on the operating environment by the apparatus. The disclosed example apparatus and methods may also beneficially increase the amount of moisture that may be evacuated from a receptacle of the apparatus in a shorter period of time. Another advantage of the disclosed example apparatus and methods may include more even heat distribution in the food waste.

Example Architecture

FIG. 1 is a block diagram showing an operating environment 100 that includes or involves, for example, an apparatus 105 for treating food waste shown in detail in FIGS. 3-23 and described below. Method 300 in FIG. 24 described below shows an embodiment of a method that can be implemented within this operating environment 100.

Figure 2:
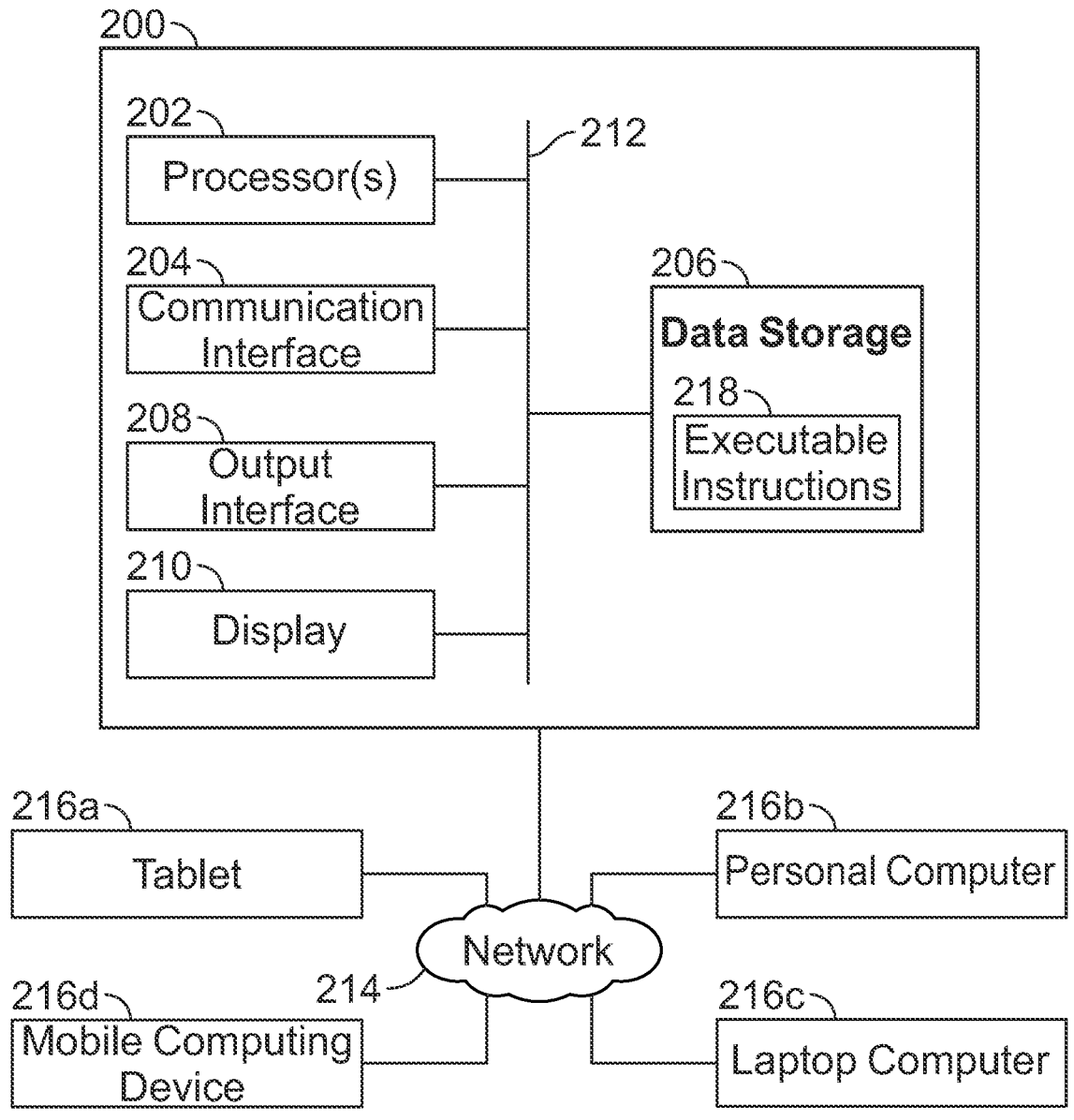
FIG. 2 depicts a block diagram of a computing device and a computer network, according to an example implementation.

FIG. 2 is a block diagram illustrating an example of a computing device 200, according to an example implementation, that is configured to interface with operating environment 100, either directly or indirectly. The computing device 200 may be used to perform functions of the method shown in FIG. 24 and described below. The computing device 200 has a processor(s) 202, and also a communication interface 204, data storage 206, an output interface 208, and a display 210 each connected to a communication bus 212. The computing device 200 may also include hardware to enable communication within the computing device 200 and between the computing device 200 and other devices (e.g. not shown). The hardware may include transmitters, receivers, and antennas, for example.

The communication interface 204 may be a wireless interface and/or one or more wired interfaces that allow for both short-range communication and long-range communication to one or more networks 214 or to one or more remote computing devices 216 (e.g., a tablet 216a, a personal computer 216b, a laptop computer 216c and a mobile computing device 216d, for example). Such wireless interfaces may provide for communication under one or more wireless communication protocols, such as Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wired interfaces may include Ethernet interface, a Universal Serial Bus (USB) interface, or similar interface to communicate via a wire, a twisted pair of wires, a coaxial cable, an optical link, a fiber-optic link, or other physical connection to a wired network. Thus, the communication interface 204 may be configured to receive input data from one or more devices and may also be configured to send output data to other devices.

The communication interface 204 may also include a user-input device, such as a keyboard, a keypad, a touch screen, a touch pad, a computer mouse, a track ball and/or other similar devices, for example.

The data storage 206 may include or take the form of one or more computer-readable storage media that can be read or accessed by the processor(s) 202. The computer-readable storage media can include volatile and/or non-volatile storage components, such as optical, magnetic, organic, or other memory or disc storage, which can be integrated in whole or in part with the processor(s) 202. The data storage 206 is considered non-transitory computer readable media. In some examples, the data storage 206 can be implemented using a single physical device (e.g., one optical, magnetic, organic or other memory or disc storage unit), while in other examples, the data storage 206 can be implemented using two or more physical devices.

The data storage 206 thus is a non-transitory computer readable storage medium, and executable instructions 218 are stored thereon. The instructions 218 include computer executable code. When the instructions 218 are executed by the processor(s) 202, the processor(s) 202 are caused to perform functions. Such functions include, but are not limited to, operating the food dehydrator apparatus disclosed herein.

The processor(s) 202 may be a general-purpose processor or a special purpose processor (e.g., digital signal processors, application specific integrated circuits, etc.). The processor(s) 202 may receive inputs from the communication interface 204, and process the inputs to generate outputs that are stored in the data storage 206 and output to the display 210. The processor(s) 202 can be configured to execute the executable instructions 218 (e.g., computer-readable program instructions) that are stored in the data storage 206 and are executable to provide the functionality of the computing device 200 described herein.

The output interface 208 outputs information to the display 210 or to other components as well. Thus, the output interface 208 may be similar to the communication interface 204 and can be a wireless interface (e.g., transmitter) or a wired interface as well. The output interface 208 may send commands to one or more controllable devices, for example.

The computing device 200 shown in FIG. 2 may also be representative of a local computing device 200a in operating environment 100, for example, in communication with food dehydrator apparatus 105. This local computing device 200a may perform one or more of the steps of the method 300 described below, may receive input from a user, and/or may send image data and user input to computing device 200 to perform all or some of the steps of method 300.

FIG. 24 shows a flowchart of an example method 300 to determine a time-versus-temperature profile in the interior cavity of the receptacle and to determine that this profile has met preset criteria to determine a suspension time for a dehydration cycle to process food waste, according to an example implementation. Method 300 shown in FIG. 24 presents an example of a method that could be used with the computing device 200 of FIG. 2, for example. In some instances, components of the apparatus 105 may be configured to perform the functions such that the components are configured and structured with hardware and/or software to enable such performance. Components of the apparatus 105 may be arranged to be adapted to, capable of, or suited for performing the functions, such as when operated in a specific manner. Method 300 may include one or more operations, functions, or actions as illustrated by one or more of blocks 305-340. Although the blocks are illustrated in a sequential order, some of these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of the present examples. In this regard, each block represents a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time such as register memory, processor cache and Random Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block in FIG. 24, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

Example Apparatus for Treating Food Waste

As used herein, "food waste" refers to raw or cooked food. For example, food waste may be generated in large quantities in cafeterias and kitchens in various operating environments, including schools, prisons, and hospitals, that can be beneficially dehydrated into livestock feed or compost.

As used herein, "dehydrated food waste" generated by the apparatus and methods disclosed herein is in coarse pellet or granular form.

As used herein, "serrated" refers to a notched or saw-like edge of the various paddles.

As used herein, a "beveled angle" refers to a sharp or knife-like edge for the various paddles.

As used herein "electrically coupled" refers to coupling using a conductor, such as a wire or a conductible trace, as well as inductive, magnetic, and wireless couplings.

In a first aspect, shown in FIGS. 3-23, an apparatus 105 for treating food waste, includes a receptacle 110 having a bottom support 115, a top support 120, and a cylindrical sidewall 125 extending therebetween. The receptacle 110 has an interior cavity 111. The top support 120 has a first opening 121 configured to receive the food waste, and the bottom support 115 has a first opening 116 to release dehydrated food waste. A load door 130 is coupled to the first opening 121 in the top support 120. A shaft 135 is rotatably arranged concentrically within the interior cavity 111 of the receptacle 110 and extending through a second opening 117 in the bottom support 115 of the receptacle 110 and through a second opening 122 in the top support 120 of the receptacle 110 such that the shaft 135 is oriented vertically. A gear motor 140 is coupled to the shaft 135 via one or more gears 136, a roller chain, or a drive belt. In one optional implementation, the gear motor 140 is configured to operate in a forward mode and in a reverse mode.

The apparatus 105 also includes a first plurality of paddles 145 each having a first end 146 coupled to a first hub 150 that is disposed concentrically about the shaft 135 in a spaced-apart arrangement. The first plurality of static paddles 145 each have a second end 147 extending radially from the first hub 150 such that the second end 147 is coupled to the cylindrical sidewall 125 of the receptacle 110. The apparatus 105 further includes a second plurality of paddles 155 each having a first end 156 coupled to a second hub 160 that is disposed concentrically about the shaft 135 in a spaced-apart arrangement below the first hub 150. The second plurality of static paddles 155 each have a second end 157 extending radially from the second hub 160 such that the second end 157 is coupled to the cylindrical sidewall 125 of the receptacle 110. The first and the second plurality of paddles 145, 155 are configured to be static.

Figure 9:
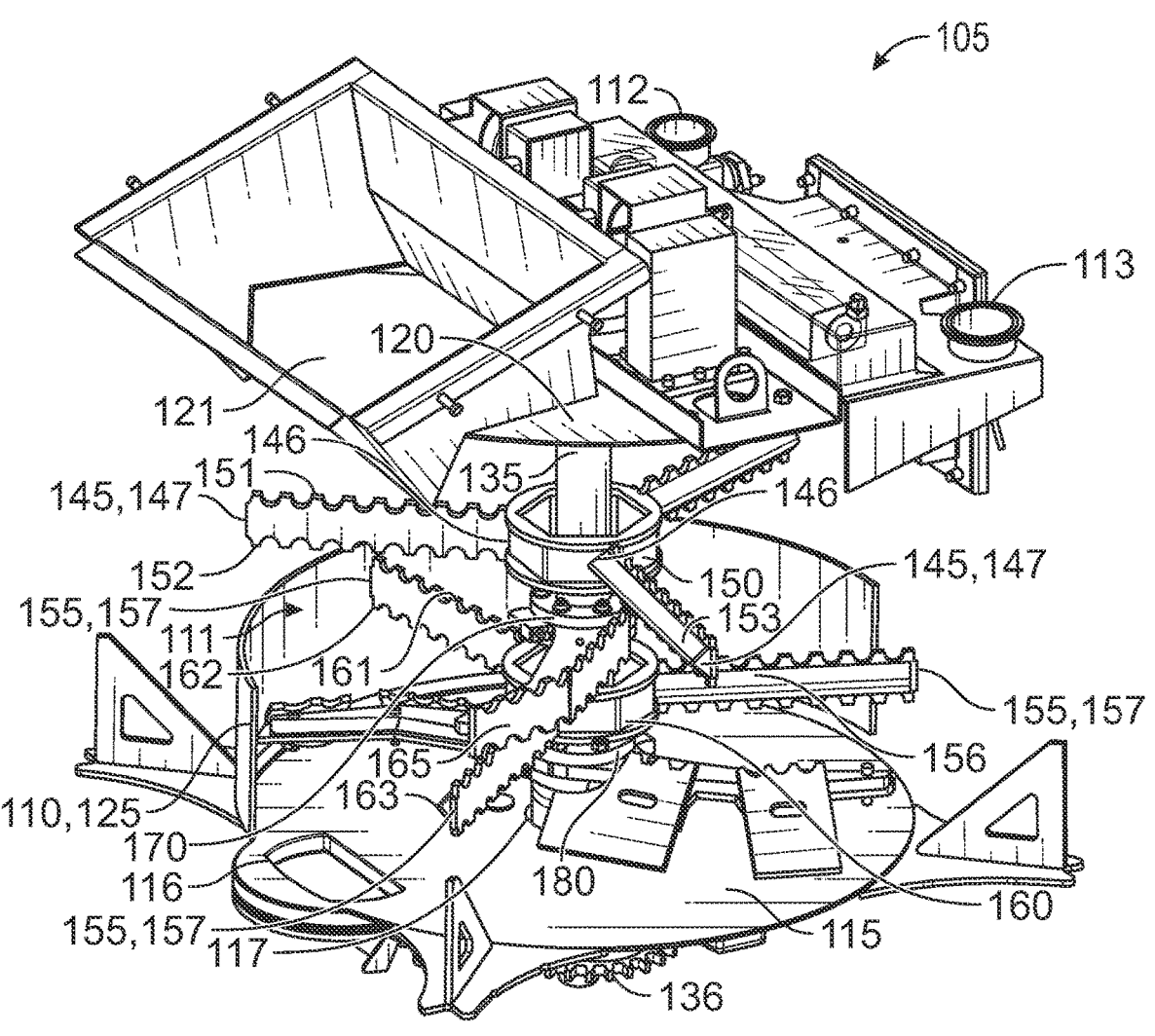
FIG. 9 depicts a partial side perspective view of the apparatus, according to the example implementation of FIG. 7.
Figure 10:
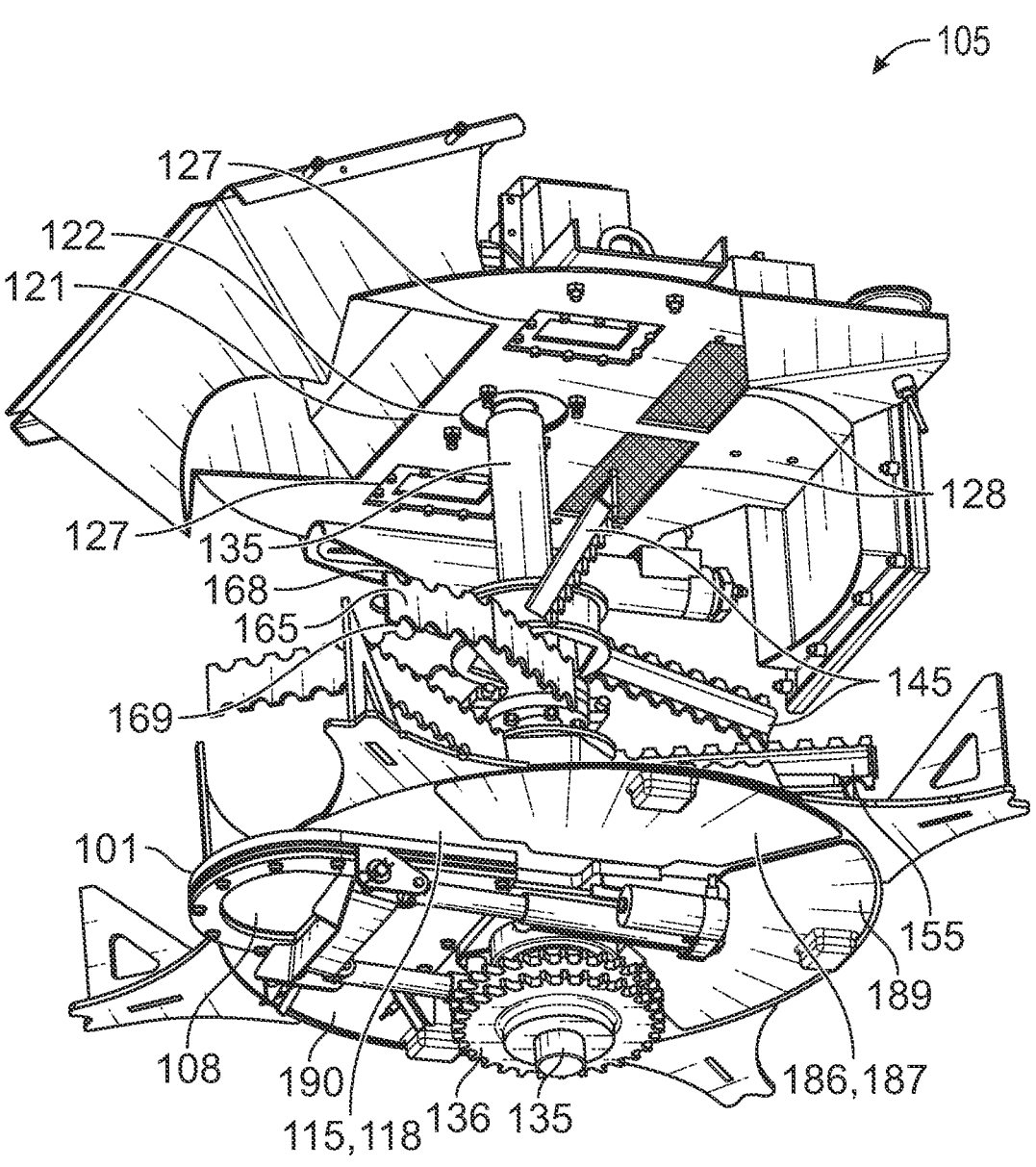
FIG. 10 depicts a partial bottom cross-sectional view of the apparatus, according to an example implementation.
Figure 11:
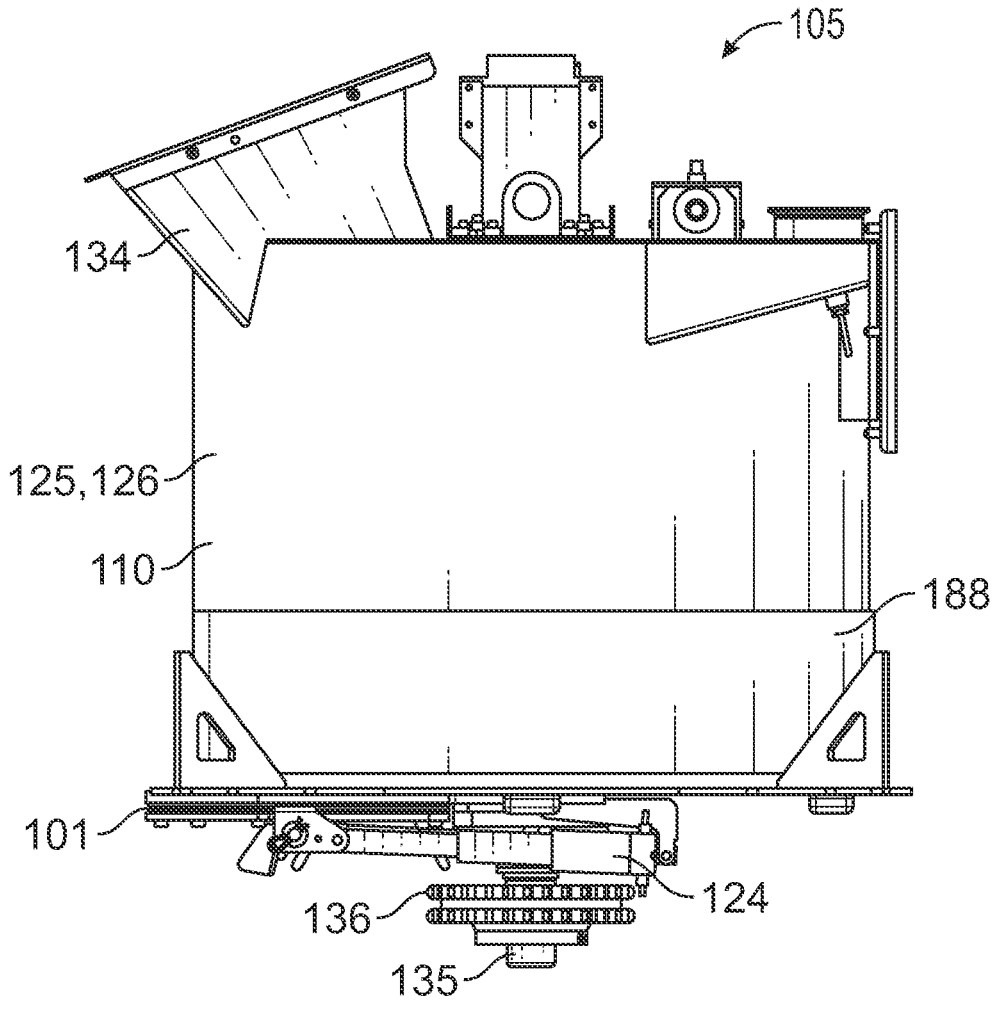
FIG. 11 depicts a side view of the apparatus, according to an example implementation.
Figure 14:
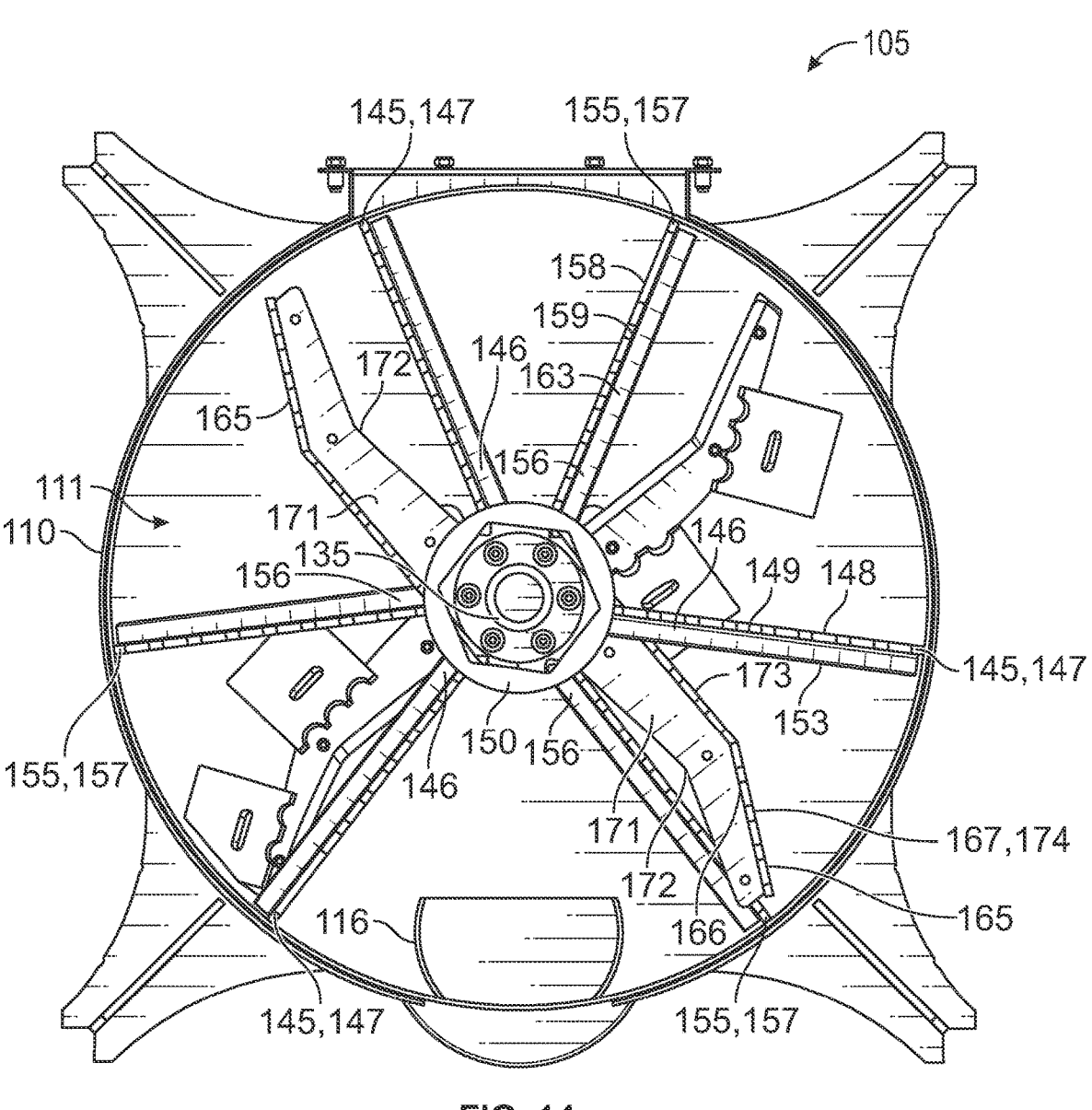
FIG. 14 depicts a bottom view of the apparatus, according to an example implementation.
Figure 15:
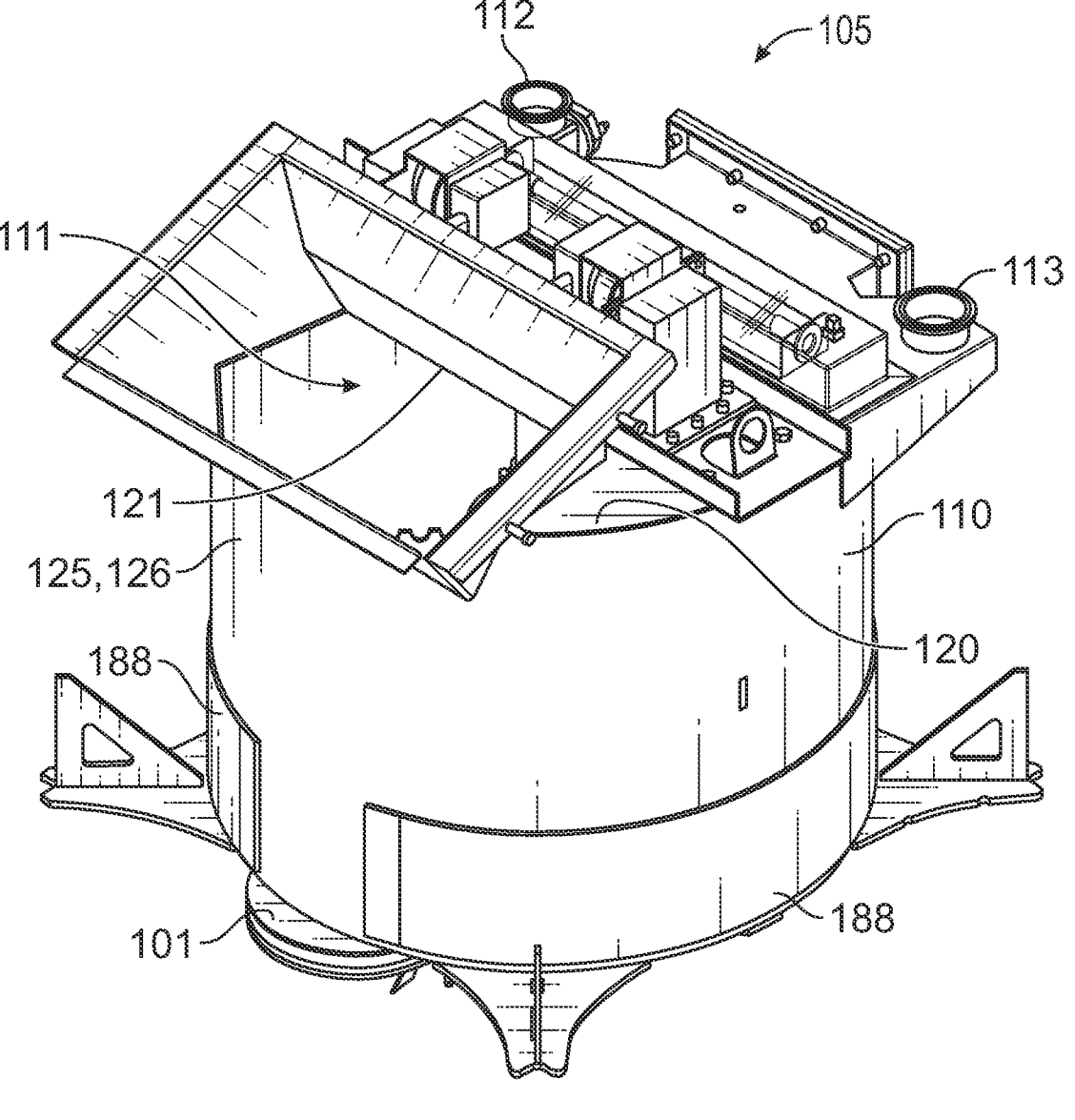
FIG. 15 shows a front perspective view of the apparatus, according to an example implementation.
Figure 16:
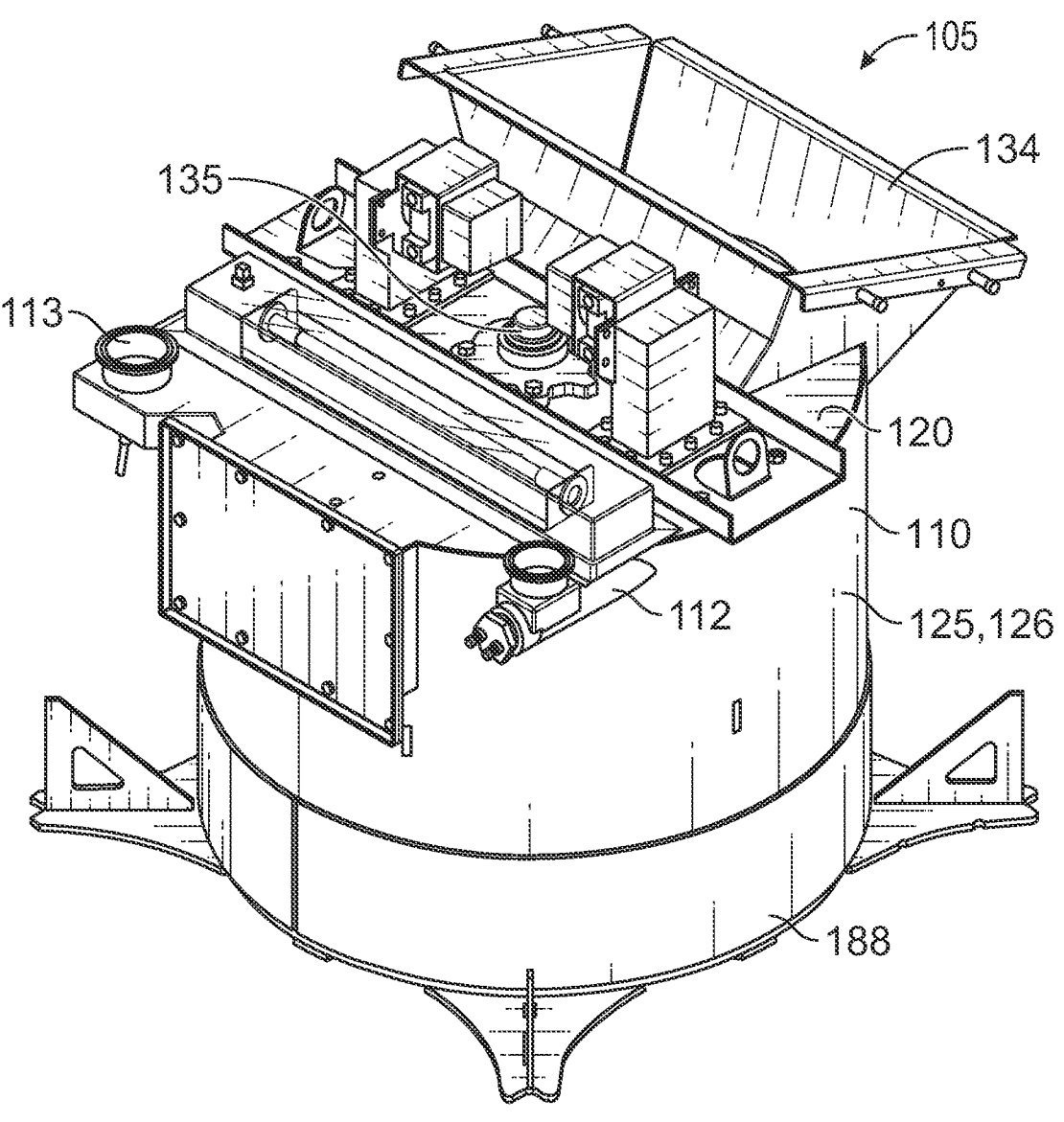
FIG. 16 shows a rear perspective view of the apparatus, according to an example implementation.

In an optional implementation, the first and the second plurality of paddles 145, 155 each have a front surface 148, 158 and an opposing back surface 149, 159 extending between a top edge 151, 161 and a bottom edge 152, 162 such that the front surface 148, 158 is arranged vertically relative to the bottom support 115 of the receptacle 110. Here, the top edge 151, 161 of each of the first and the second plurality of paddles 145, 155 is serrated, as shown in FIGS. 9-10 and 14. In a further optional implementation, the bottom edge 152, 162 of each of the first and the second plurality of paddles 145, 155 is serrated, as shown in FIGS. 9-10.

In one optional implementation, the apparatus 105 includes a wedge support 153, 163 that is coupled to the back surface 149, 159 of each of the first and the second plurality of paddles 145, 155.

In one optional implementation, shown in FIG. 14, the first plurality of paddles 145 includes three paddles arranged 120 degrees apart about the first hub 150, and the second plurality of paddles 155 includes three paddles arranged 120 degrees apart about the second hub 160. In this implementation, the first plurality of paddles 145 and the second plurality of paddles 155 are offset from each other by 60 degrees.

The apparatus 105 further includes a third plurality of paddles 165 coupled to a third hub 170 that is coupled to the shaft 135 between the first hub 150 and the second hub 160. And the apparatus 105 includes a fourth plurality of paddles 175 coupled to a fourth hub 180 that is coupled to the shaft 135 between the second hub 160 and the bottom surface 115 of the receptacle 110. The third plurality of paddles 165 and the fourth plurality of paddles 175 are configured to rotate with the shaft 135.

Figure 4:
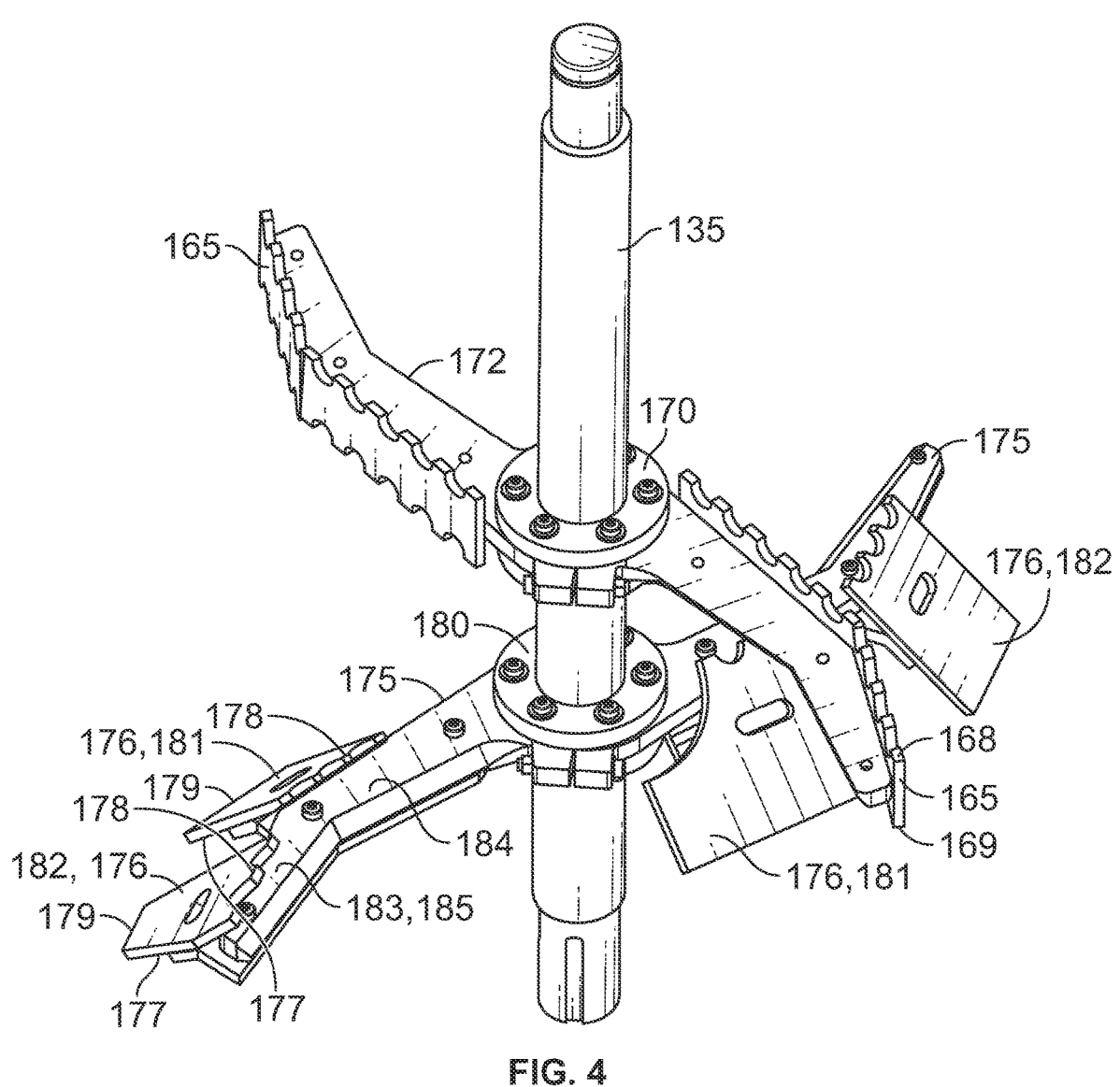
FIG. 4 depicts a top perspective view of the third and fourth plurality of paddles disposed on the shaft, according to the example implementation of FIG. 3.
Figure 5:
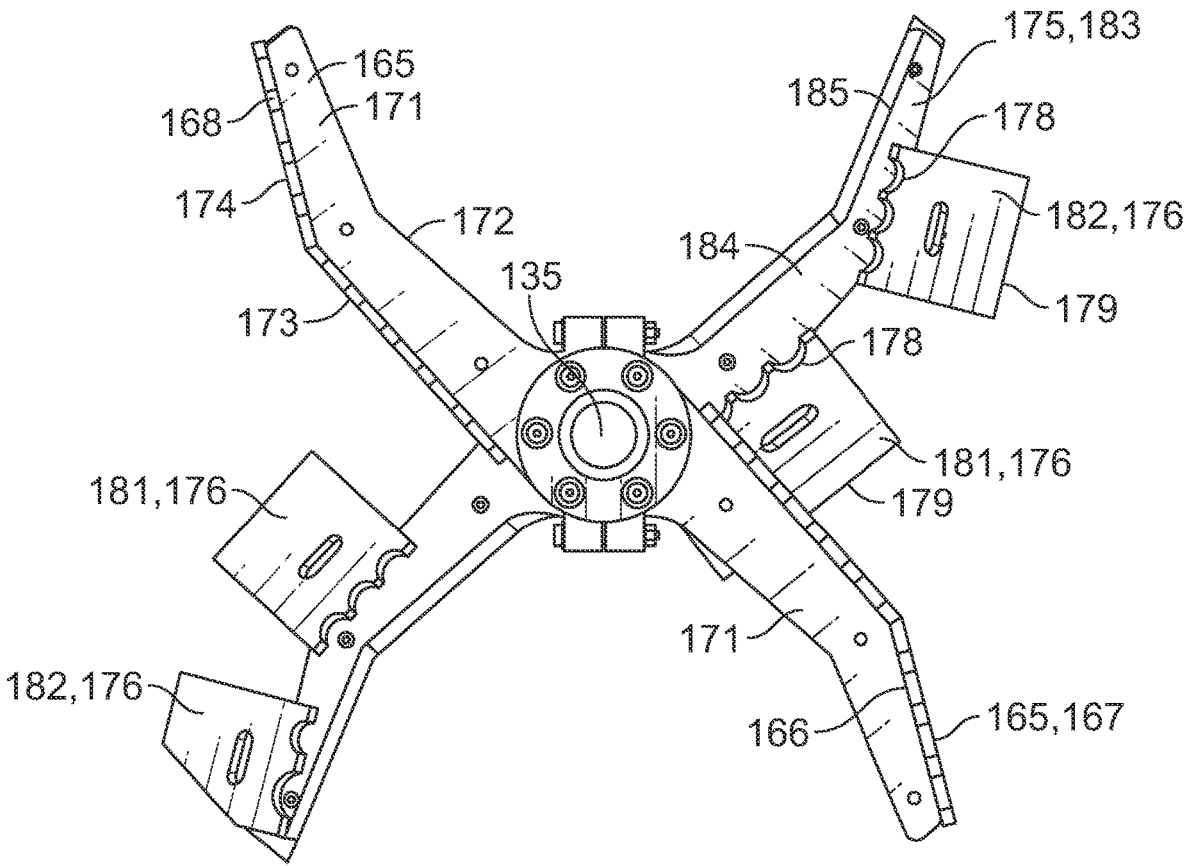
FIG. 5 depicts a top view of the third and fourth plurality of paddles disposed on the shaft, according to an example implementation.

In another optional implementation, shown in FIGS. 4-5, the third plurality of paddles 165 each include (i) a front surface 166 and an opposing back surface 167 extending between a top edge 168 and a bottom edge 169 such that the front surface 166 is arranged vertically relative to the bottom support 115 of the receptacle 110, and (ii) a support arm 171 coupled to the front surface 166. In this implementation, the support arm 171 has a beveled front edge 172. The third plurality of paddles 165 each have an inner segment 173 and an outer segment 174. And the outer segment 174 is arranged at a forward angle relative to the inner segment 173 such that each of the third plurality of paddles 165 is curved and thereby configured to move the food waste toward the shaft 135 when the third plurality of paddles 165 is moving in a forward direction of rotation.

Figure 3:
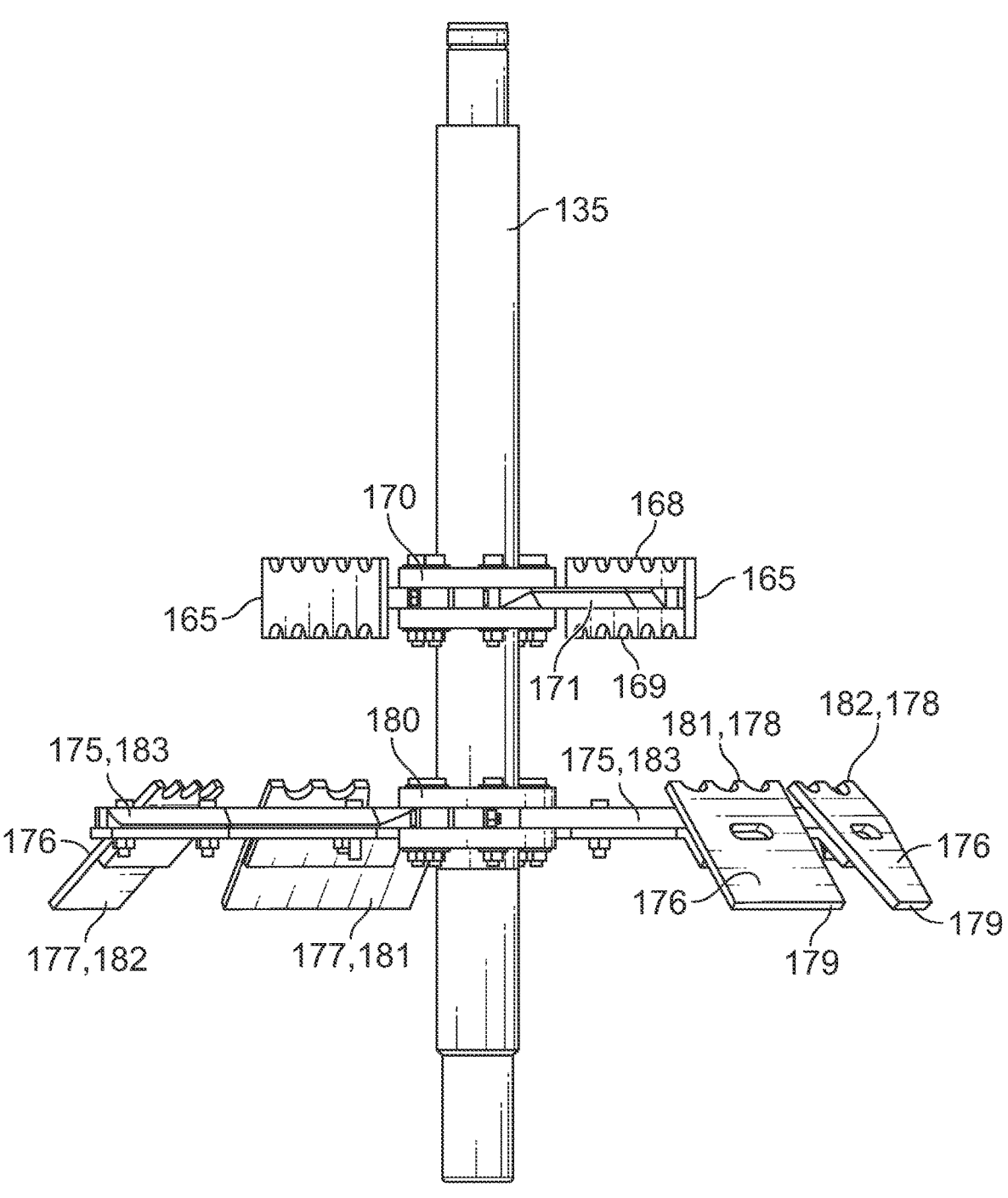
FIG. 3 depicts a side view of the third and fourth plurality of paddles disposed on the shaft, according to an example implementation.

In a further optional implementation, the top edge 168 of each of the third plurality of paddles 165 has a beveled angle and/or is serrated, as shown in FIGS. 3-5. In still another optional implementation, the bottom edge 169 of each of the third plurality of paddles 165 has a beveled angle and/or is serrated.

In another optional implementation, the third plurality of paddles 165 includes two paddles arranged on opposing sides of the third hub 170, as shown in FIGS. 3-5.

In one optional implementation, shown in FIGS. 3-5, the fourth plurality of paddles 175 each include an inner paddle portion 181 and an outer paddle portion 182 each having a front surface 176 and an opposing back surface 177 extending between a top edge 178 and a bottom edge 179. The front surface 176 of each of the fourth plurality of paddles 175 is angled toward the top surface 120 of the receptacle 110 and the bottom edge 179 is arranged as a leading edge and the top edge 178 is arranged as a trailing edge in a forward direction of rotation. The fourth plurality of paddles 175 each further include a support arm 183 having an inner segment 184 and an outer segment 185. The inner segment 184 of the support arm 183 is coupled to the back surface 177 of the inner paddle portion 181 and the outer segment 185 of the support arm 183 is coupled to the back surface 177 of the outer paddle portion 182. The outer segment 185 of the support arm 183 is arranged at a lag angle relative to the inner segment 184 such that each of the fourth plurality of paddles 175 is curved such that the inner paddle portion 181 is configured to advance the food waste forward and the outer paddle portion 182 is configured to advance the food waste toward and/or upward along the cylindrical sidewall 125 of the receptacle 110.

In a further optional implementation, shown in FIGS. 3-5, the top edge 178 of each of the inner paddle portions 181 and the outer paddle portions 182 of the fourth plurality of paddles 175 has a beveled angle and/or is serrated.

In another optional implementation, shown in FIGS. 3-5, the third plurality of paddles 165 includes two paddles arranged on opposing sides of the third hub 170. And the fourth plurality of paddles 175 includes two paddles arranged on opposing sides of the fourth hub 180. In this implementation, the third plurality of paddles 165 and the fourth plurality of paddles 175 are offset from each other by 90 degrees, as shown in FIG. 5.

In addition, the apparatus 105 further includes at least one heat source 186 comprising one or more of (i) at least one heating pad 187 coupled to the bottom support 115 and/or the cylindrical sidewall 125 of the receptacle 110, (ii) a heat exchanger 191 coupled to the receptacle 110 via an inlet opening 112 and an outlet opening 113, and (iii) at least one microwave 127 coupled to the top support 120 and configured to emit microwaves into the interior cavity 111 of the receptacle 110.

In one optional implementation, the at least one heat source 186 includes a first heating pad 187 coupled to an exterior 118 of the bottom support 115 of the receptacle 110 and a second heating pad 188 coupled to an exterior 126 of the cylindrical sidewall 125 at a location between the bottom support 115 and a midpoint along a height of the cylindrical sidewall 125. In one alternative implementation, as shown in FIGS. 12-13 and 15-16, the at least one heat source 186 includes a plurality of heating pads 187, 189, 190 coupled to an exterior 118 of the bottom support 115 of the receptacle 110 and a heating pad coupled 188 to an exterior 126 of the cylindrical sidewall 125 adjacent to the bottom support 115.

Figure 12:
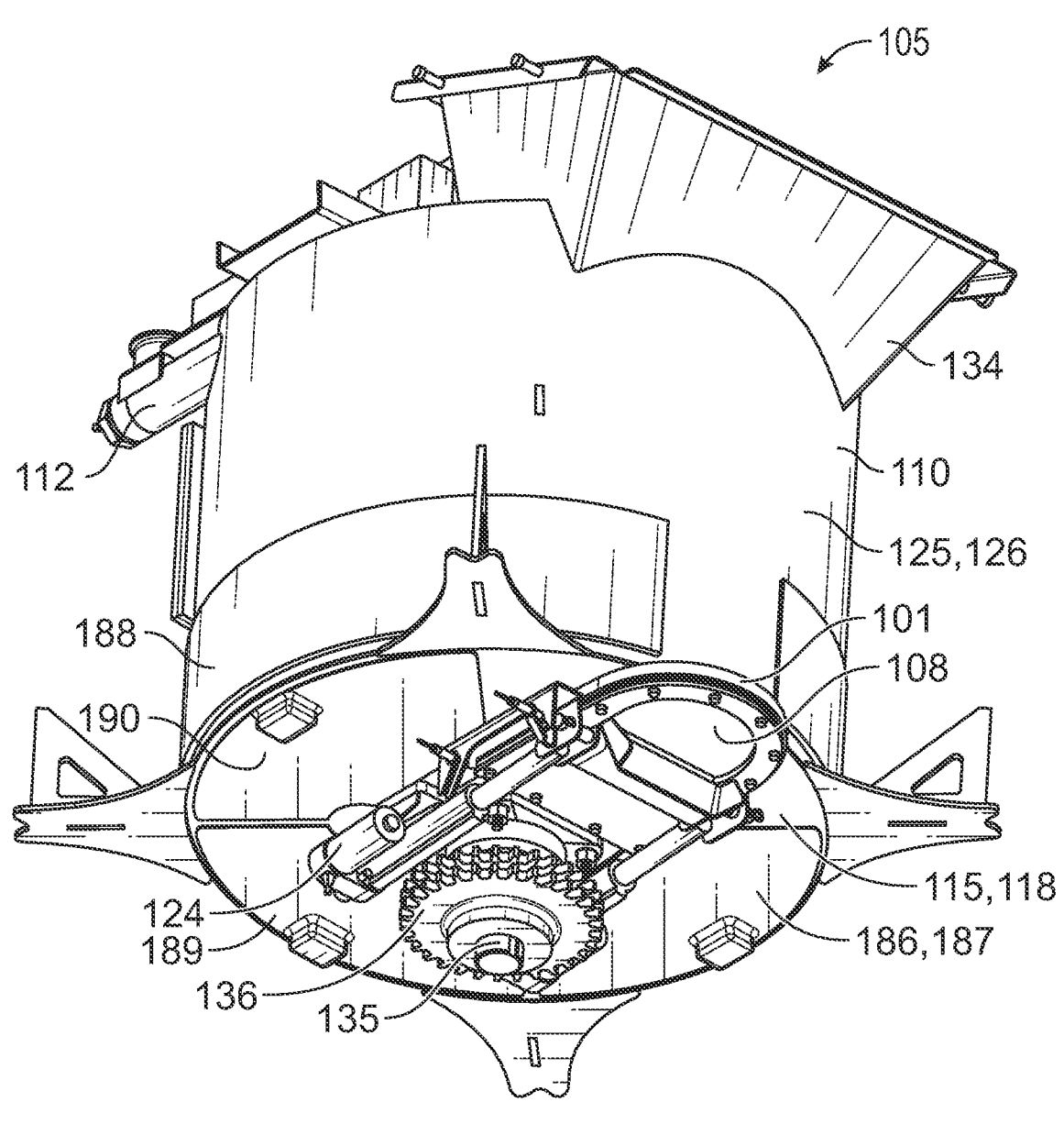
FIG. 12 depicts a bottom perspective view of the apparatus, according to an example implementation.
Figure 13:
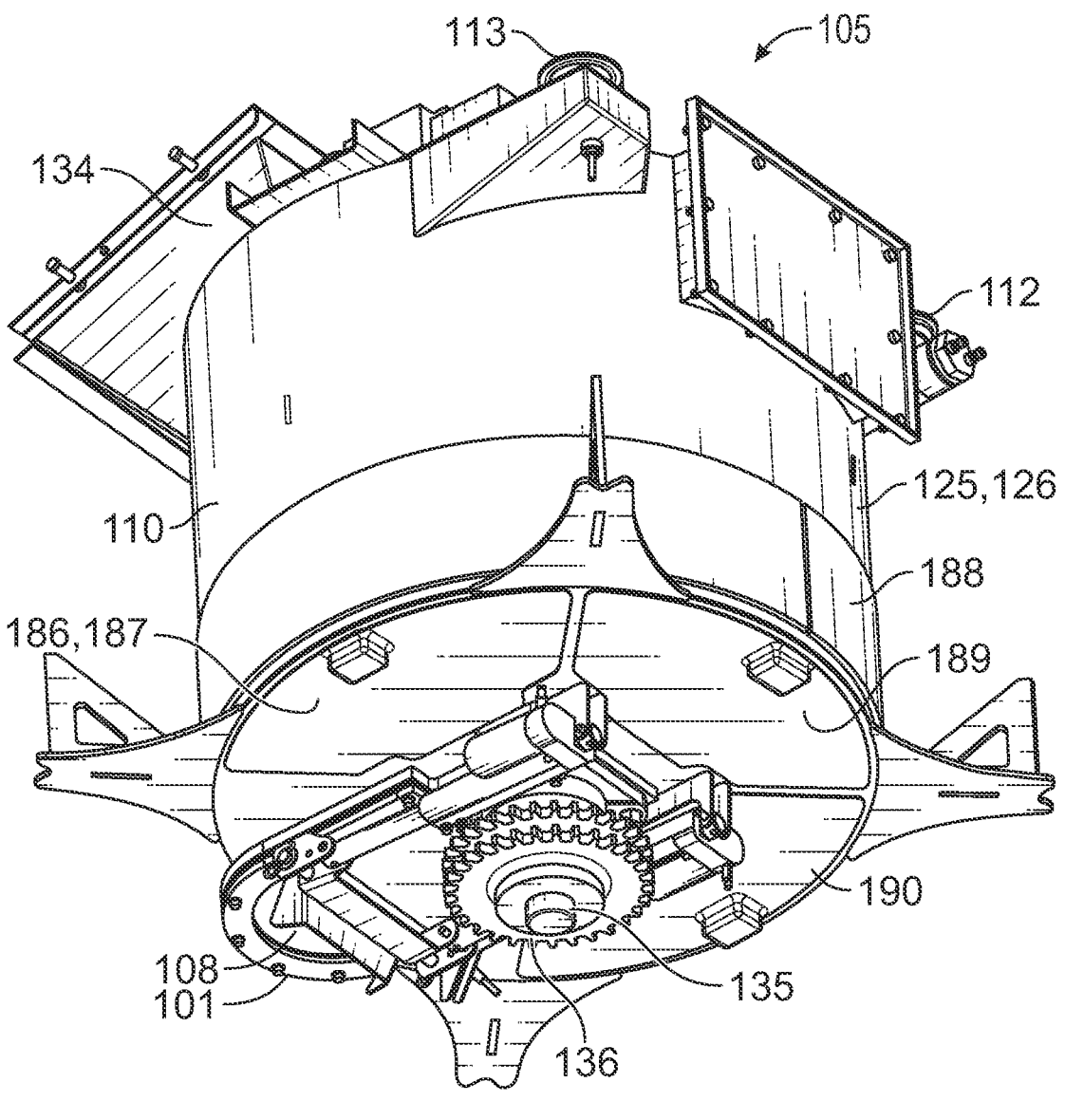
FIG. 13 depicts a bottom perspective view of the apparatus, according to an example implementation.

In another alternative implementation, shown in FIGS. 10 and 12, the at least one heat source 186 includes three heating pads 187, 189, 190 coupled to the exterior 118 of the bottom support 115 and a heating pad 188 coupled to the exterior 126 of the cylindrical sidewall 125 adjacent to the bottom support 115. In this alternative implementation, the three heating pads 187, 189, 190 are each arranged to cover a substantial portion of a quadrant of the circular bottom support 115. And the three heating pads 187, 189, 190 are further arranged to accommodate the gate 101 (discussed below) that is arranged in a fourth quadrant underneath the first opening 116 in the bottom support 115 and to accommodate the shaft 135 and a drive mechanism.

Figure 17:
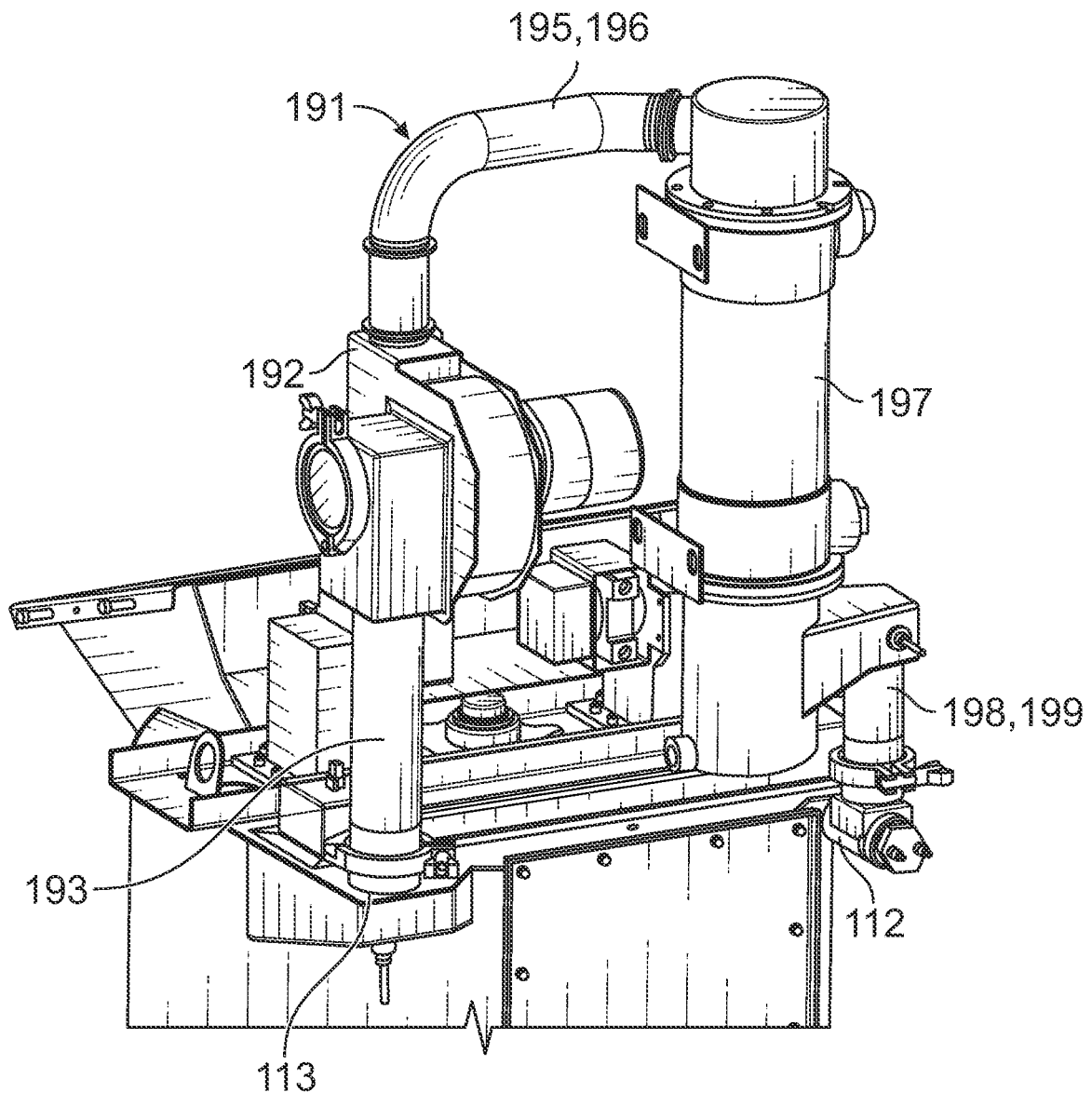
FIG. 17 shows a heat exchanger, according to an example implementation.
Figure 18:
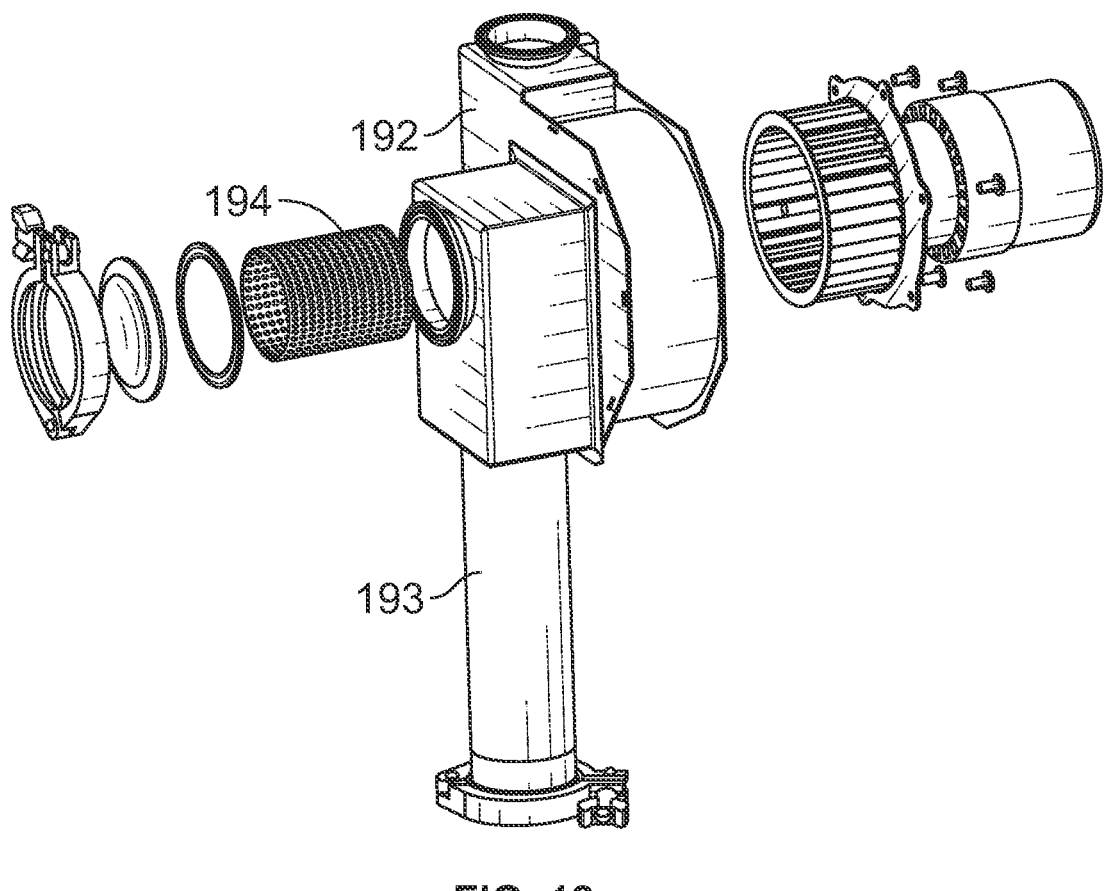
FIG. 18 shows an air blower, according to an example implementation.
Figure 19:
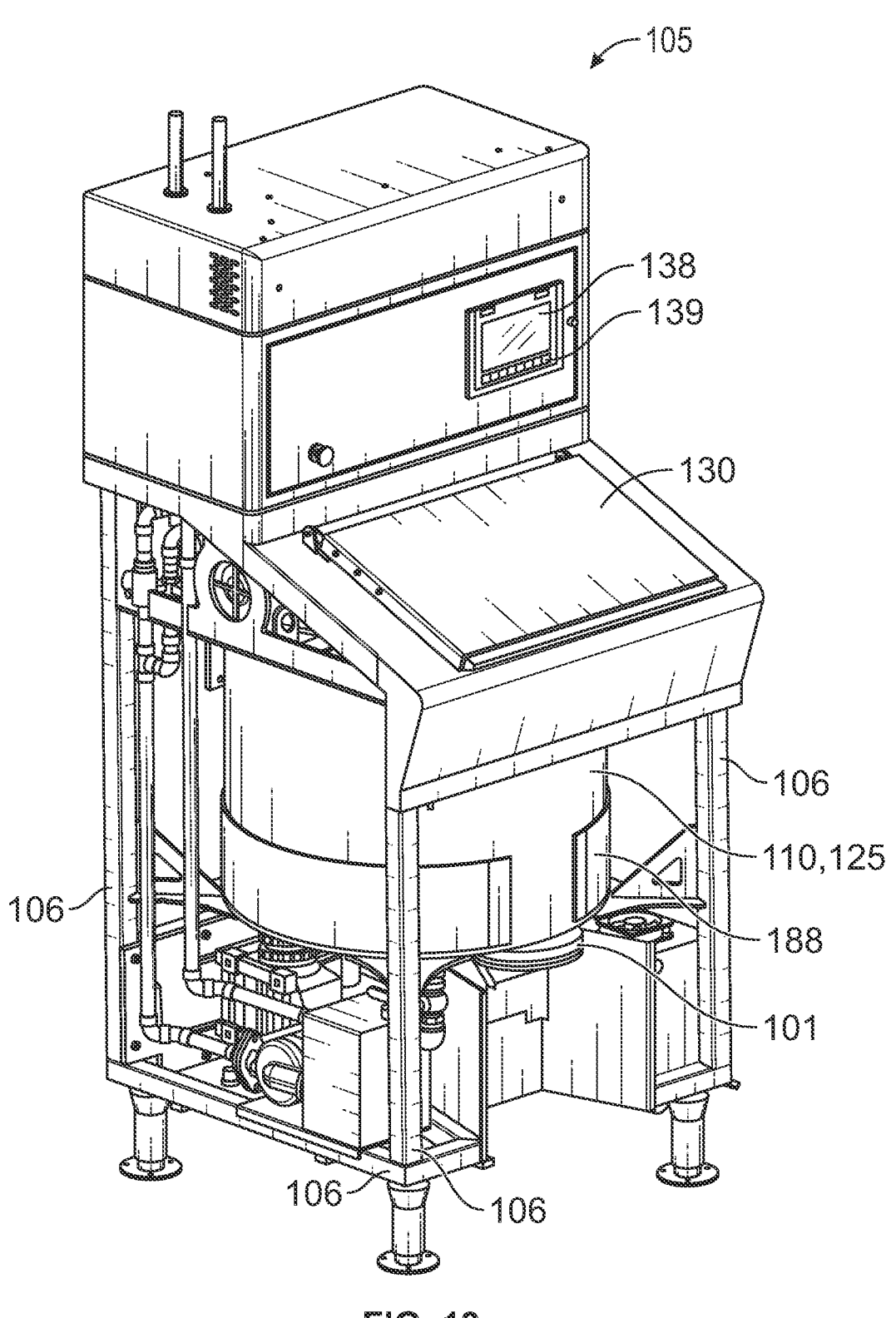
FIG. 19 shows a front perspective view, according to an example implementation.
Figure 20:
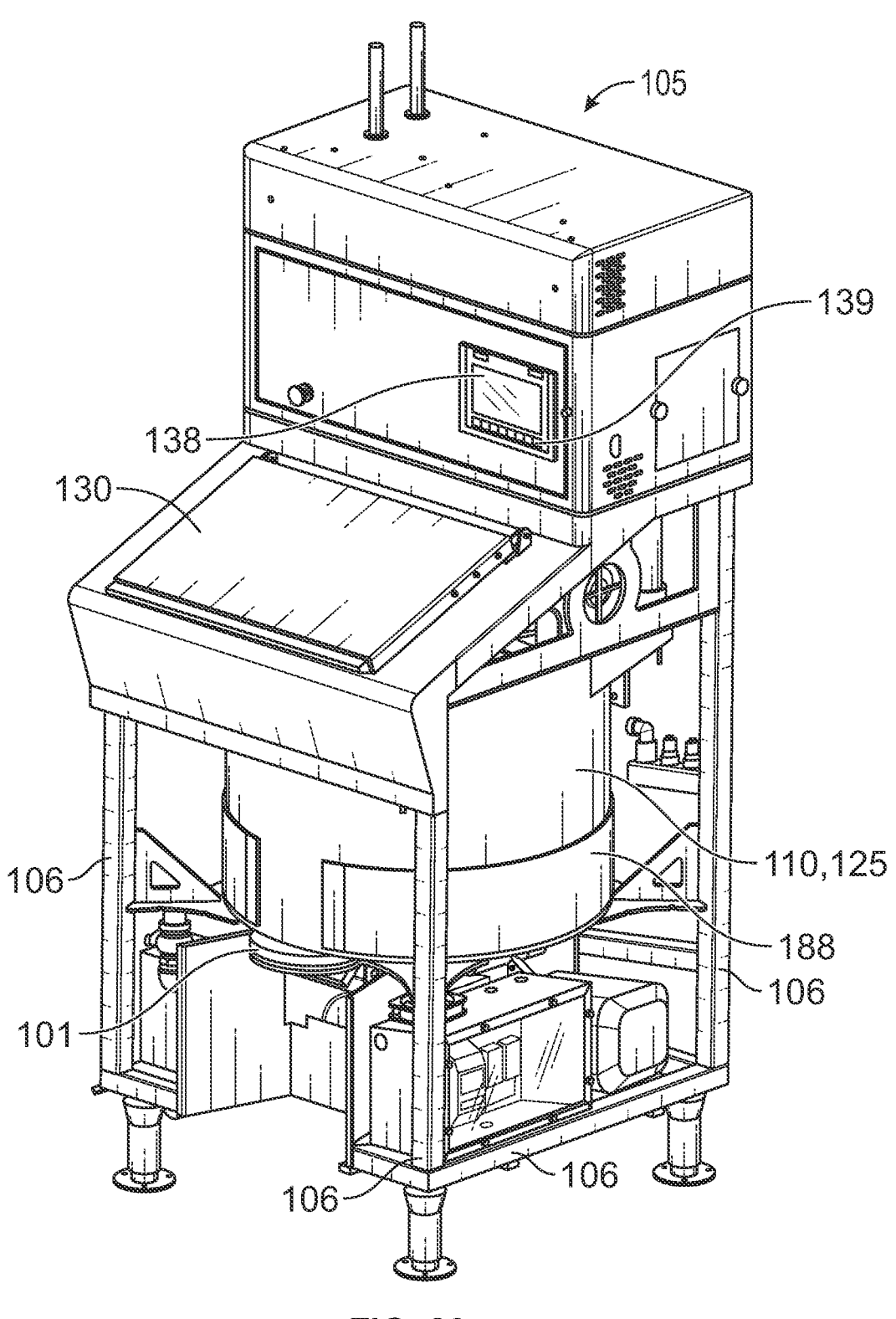
FIG. 20 shows a front perspective view, according to an example implementation.

In one optional implementation, shown in FIGS. 17-18, the heat exchanger 191 includes an air blower 192 that is coupled to the outlet opening 113 via a first conduit 193 that is configured to receive moist air from the interior cavity 111 of the receptacle 110. The air blower 192 includes a circular filter 194 configured to separate particles from the moist air. The heat exchanger 191 also includes a second conduit 195 that is coupled to the air blower 192 and is configured to separate water from the moist air via a water-cooled pipe 196 contained therein. The heat exchanger 191 further includes a drainage pipe 197 that is coupled to the second conduit 195 and that is configured to receive the water that is separated from the moist air. And the heat exchanger 191 includes a third conduit 198 that is coupled to the second conduit 195 and that is arranged to return air to the interior cavity 111 of the receptacle 110 via the inlet opening 112. The third conduit 198 includes a heating element 199 arranged therein that is configured to heat returning air. In one optional implementation, the heating element is configured to heat the returning air to a temperature ranging from 165° F. to 225° F.

In operation, the heat exchanger 191 disclosed herein utilizes water to cool the air received from the interior cavity 111 of the receptacle 110. The technical effect is to avoid imposing a heat load on the operating environment 100 occupied by the food dehydrator apparatus 105, because the water-cooled pipe 196 transfers the heat out of both the apparatus 105 and the operating environment 100 in which the apparatus 105 is disposed.

Further, during a dehydration cycle, the air in the interior cavity 111 of the receptacle 110 becomes laden with vapor. This moist air is then removed through an outlet opening 113 and advanced to the heat exchanger 191. The heat exchanger 191 removes water from the moist air. This air is then heated and returned to the receptacle 110 via an inlet opening 112. The technical effect of heating the returning air is that warmer air is capable of holding more moisture than cooler air and therefore increases the amount of moisture that may be evacuated from the receptacle 110 in a shorter period of time.

In one optional implementation, shown in FIG. 10, the at least one heat source 186 comprises at least two microwaves 127 coupled to the top support 120 on opposing sides of the shaft 135. The arrangement of the microwaves 127 in the top surface 120 along a centerline of the receptacle 110, in one this example implementation, advantageously permits the direction of the microwave radiation to be parallel to agitation of the food waste along the shaft 135. The technical effect of this arrangement is to increase uniformity in the exposure of the food waste to the microwave radiation and a more even heat distribution in the food waste. The microwaves 127 are water-cooled and more energy efficient than the air-cooled microwaves of prior art food dehydrators that require more air-conditioning. In addition, a pulse transformer to control the microwave 127 also helps to avoid additional heat load on the surrounding operating environment 100.

The apparatus 105 also includes a gate 101 coupled to the bottom support 115 of the receptacle 110. The gate 101 is configured to move between a closed position such that the gate 101 creates a watertight seal with the first opening 116 in the bottom support 115 of the receptacle 110 and an open position that permits the dehydrated food waste to exit the interior cavity 111 of the receptacle 110 through the first opening 116 in the bottom support 115.

Figure 6:
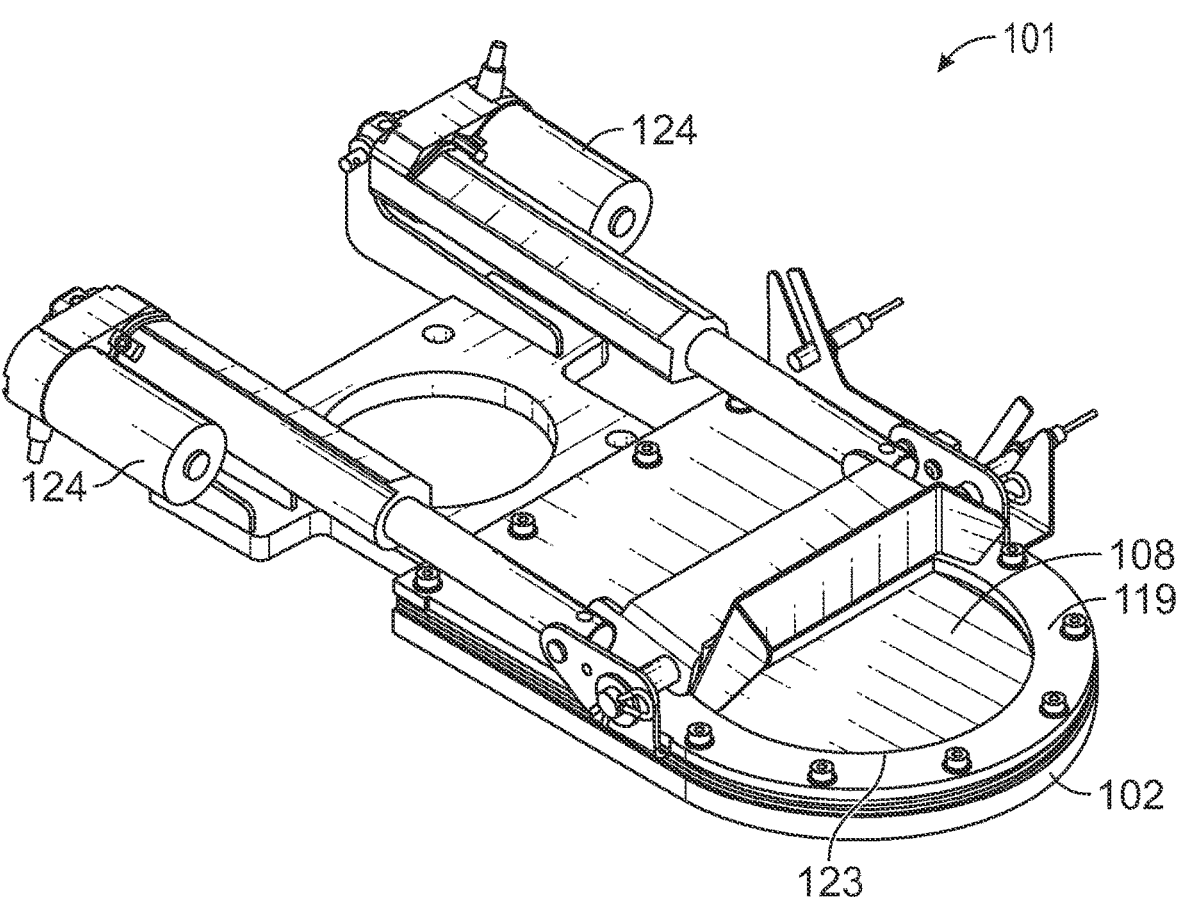
FIG. 6 depicts a bottom perspective view of the gate, according to an example implementation.
Figure 7:
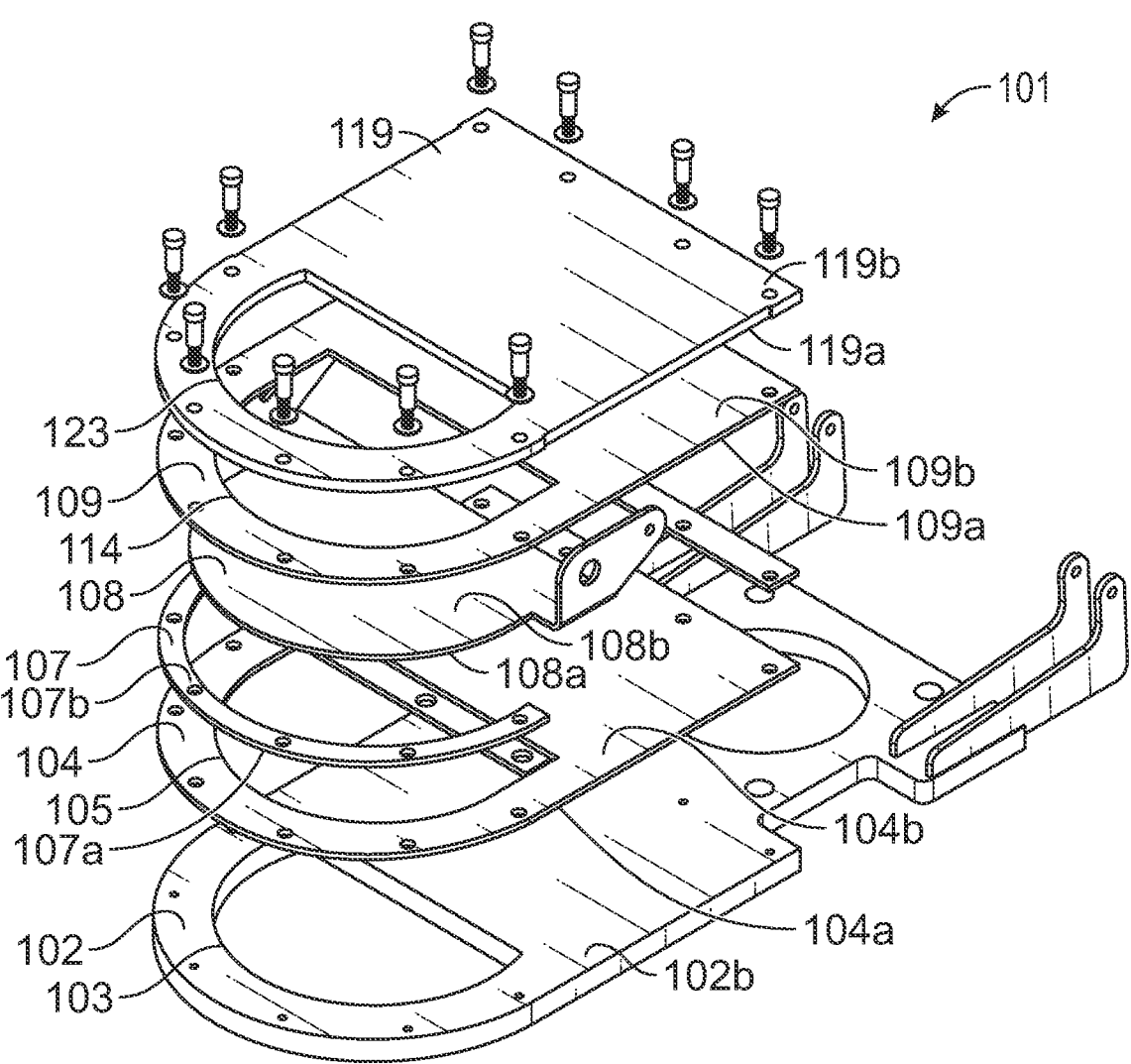
FIG. 7 depicts an exploded bottom perspective view of the gate, according to an example implementation.
Figure 8:
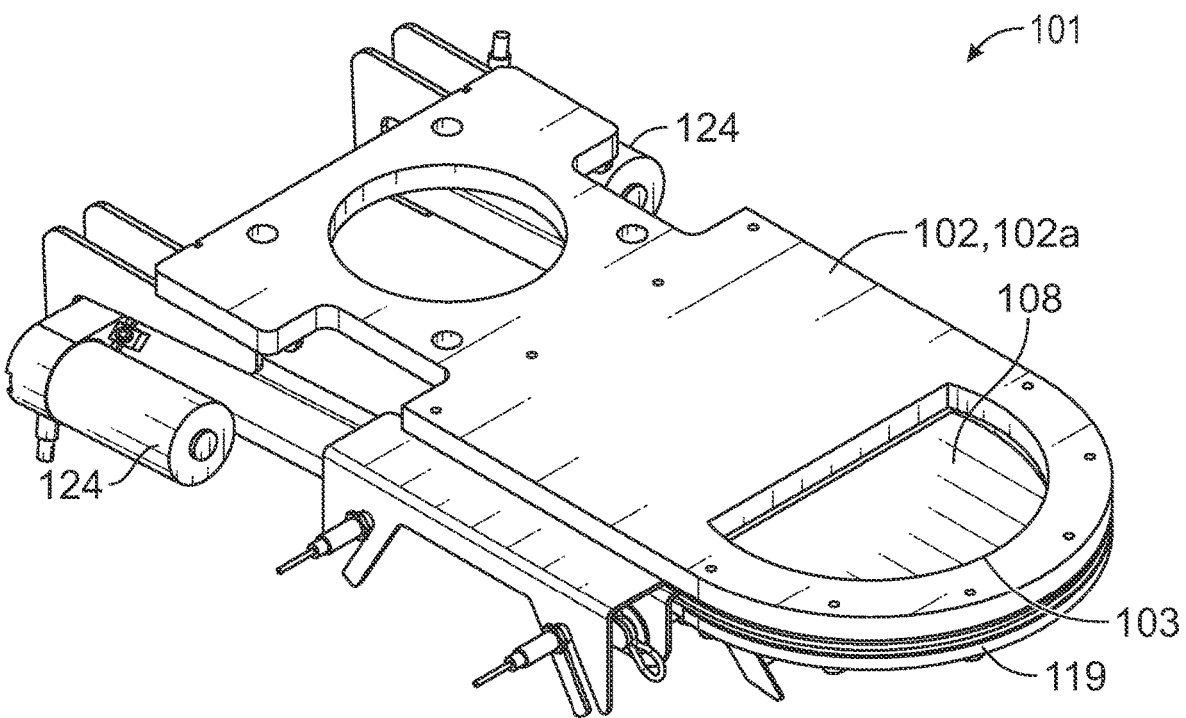
FIG. 8 depicts top perspective view of the gate, according to an example implementation.

In one optional implementation, shown in FIGS. 6-8, the gate 101 includes a first metal plate 102 having a first semicircular opening 103, and a first Teflon plate 104 having a second semicircular opening 105. A top surface 104a of the first Teflon plate 104 is coupled to a bottom surface 102b of the first metal plate 102 such that the first semicircular opening 103 is aligned with the second semicircular opening 105. The gate 101 further includes a spring washer 107 having an arc shape corresponding to a perimeter of the second semicircular opening 105 in the first Teflon plate 104. The spring washer 107 has a top surface 107a coupled to a bottom surface 104b of the first Teflon plate 104. The gate 101 also includes stainless-steel plate 108 having a semicircular shape and having a top surface 108a slidably coupled to a bottom surface 107b of the spring washer 107 and to the bottom surface 104b of the first Teflon plate 104. The gate 101 further includes a second Teflon plate 109 having a third semicircular opening 114, and a bottom surface 108b of the stainless-steel plate 108 is slidably coupled to a top surface 109a of the second Teflon plate 109. The gate 101 also includes a second metal plate 119 having a fourth semicircular opening 123, and a top surface 119a of the second metal plate 119 is coupled to a bottom surface 109b of the second Teflon plate 109.

The first, the second, the third, and the fourth semicircular openings 103, 105, 114, 123 of the gate 101 are aligned with each other. As a result of this arrangement, in the closed position of the gate 101, the stainless-steel plate 108 is arranged beneath the first opening 116 in the bottom support

115 of the receptacle 110 and the first and second semicircular openings 103, 105 and above the third and fourth semicircular openings 114, 123. And the gate 101 includes at least one electric actuator 124 coupled to the stainless-steel plate 108 and configured to move the stainless-steel plate 108 between the closed position and the open position. In the open position of the gate 101, the stainless-steel plate 108 is retracted out of alignment with the first opening 116 in the bottom support 115 of the receptacle 110, the first, the second, the third, and the fourth semicircular openings 103, 105, 114, 123.

In one optional implementation, the apparatus 105 includes at least one sensor 137 coupled to at least one of the bottom support 115 and the gate 101, the at least one sensor 137 configured to determine whether the gate 101 is in the closed position or the open position.

In a further optional implementation, shown in FIG. 10, the apparatus 105 further includes at least one UV light source 128 coupled to the top support 120 and configured to emit UV wavelengths into the interior cavity 111 of the receptacle 110. The UV light source 128 advantageously emits UV wavelengths into the interior cavity 111 of the receptacle 110 to sterilize the food waste and thereby reduce viruses and bacteria present in the food waste. The UV wavelengths also may be used to mitigate odors.

In another optional implementation, the apparatus 105 further includes a plurality of temperature sensors 129 configured to measure the temperature at the bottom of the receptacle 110, to measure ambient air temperature in an operating environment 100 of the apparatus 105 external to the receptacle 110, and to measure the temperature of the air at the outlet opening 113 and at the inlet opening 112.

In one optional implementation, the apparatus 105 further includes a processor 202 electrically coupled to the gear motor 140, the at least one heat source 186, the gate 101, and the plurality of temperature sensors 129. In a further implementation, shown in FIG. 19-20, the apparatus 105 includes a display 138 and at least one user input device 139 electrically coupled to the processor.

Figure 21:
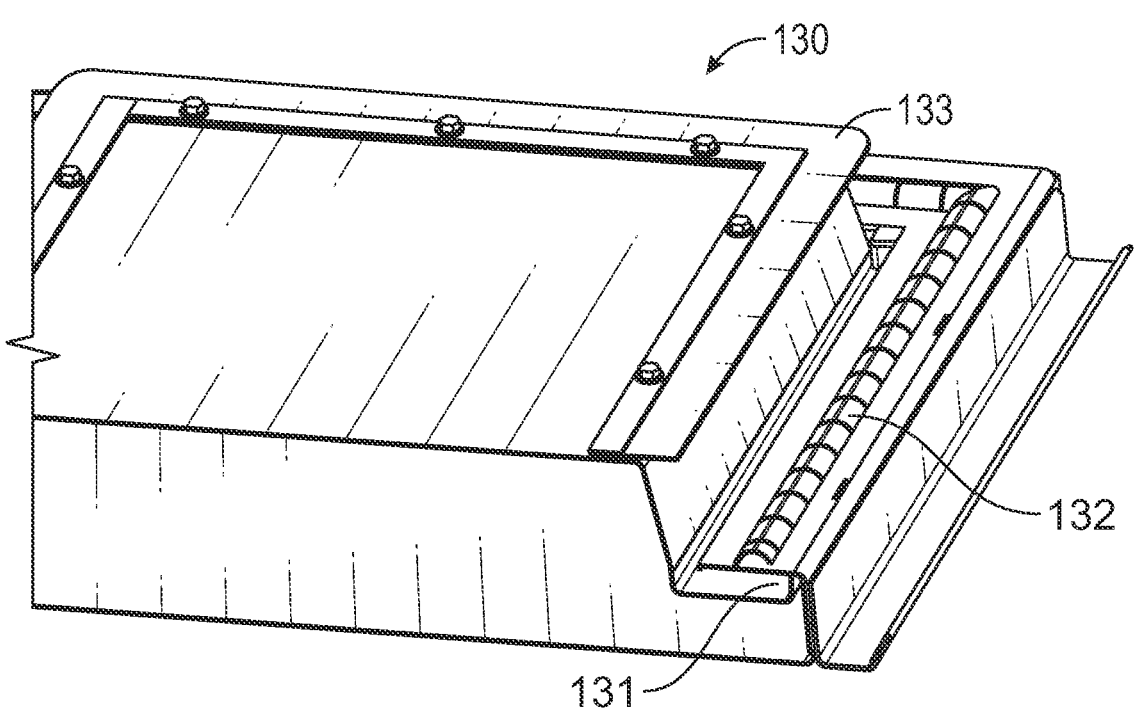
FIG. 21 shows a partial bottom perspective view of the load door, according to an example implementation.
Figure 22:
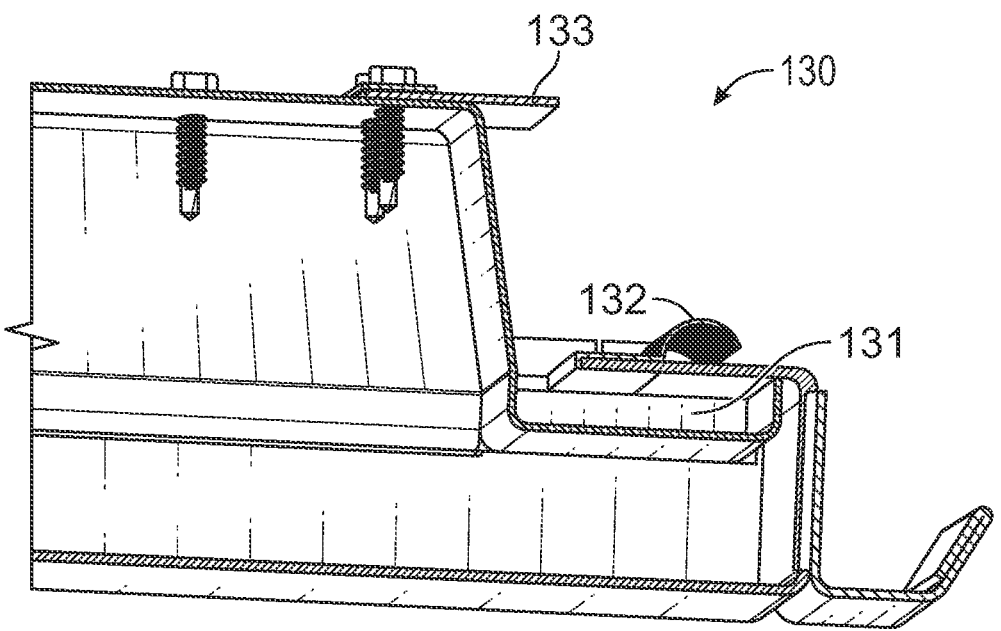
FIG. 22 shows a side cross-sectional view of the load door, according to an example implementation.
Figure 23:
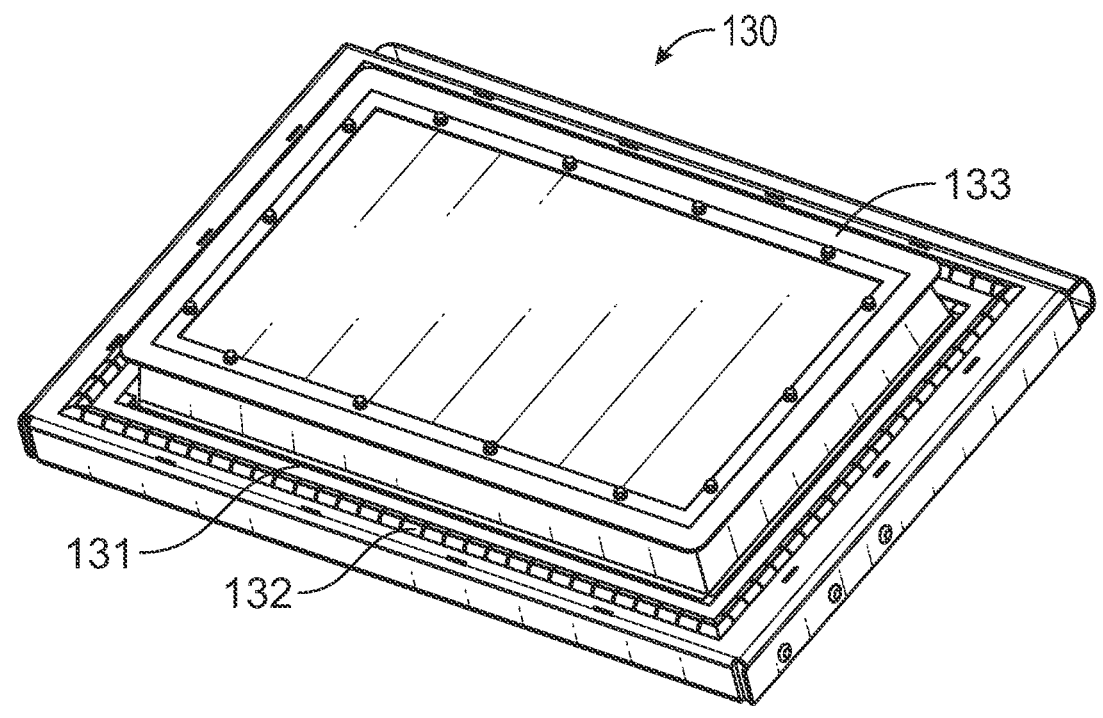
FIG. 23 shows a bottom perspective view of the load door, according to an example implementation.

In one optional implementation, shown in FIGS. 21-23, the load door 130 includes a microwave choke 131 and a metallic finger-stock gasket 132 configured to create a seal against microwaves. And the load door 130 includes a silicon gasket 133. The silicon gasket 133 has the technical effect of decreasing the escape of air and may thereby reduce odors associated with the food waste.

In one optional implementation, shown in FIGS. 9-13, the apparatus 105 further includes a load chute 134 coupled to the first opening 121 in the top support 120 and to the load door 130. The load chute 134 is disposed at a 20° angle. And the apparatus 105 includes an external housing enclosing the load chute 134, the receptacle 110, the at least one heat source 186, the gear motor 140, and the gate 101. The external housing is affixed to the frame 106 shown in FIGS. 19-20.

The vertical arrangement of the shaft 135 in the receptacle 110 relative to the ground beneficially permits a reduced apparatus footprint of 30 inches×30 inches. In addition, in one optional implementation, the semicircular shape of the gate 101 follows the contour of the receptacle 110 that permits the gate 101 to be positioned close to the edge of the receptacle 110 to aid in the reduced compact footprint of the apparatus 105. Still further, in one optional implementation, a load chute 134 that is coupled to the first opening 121 of the top support 120 and to the load door 130 at a 20° angle further contributes to this reduced footprint.

Example Methods

Referring now to FIG. 24, a method 300 is illustrated for operating the apparatus for treating food waste shown in FIGS. 3-23 and using the computing device of FIGS. 1-2. Method 300 includes, at block 305, receiving the food waste in the interior cavity 111 of the receptacle 110. Then, at block 310, the processor 202 continuously monitors a temperature in the interior cavity 111 of the receptacle 110. Next, at block 315, the shaft 135 rotates the third plurality and the fourth plurality of paddles 165, 175 and thereby mixes the food waste. Then, at block 320, the at least one heat source 186 heats the food waste to a peak temperature. Next, at block 325, the processor 202 determines that the temperature in the interior cavity 111 of the receptacle 110 has reached the peak temperature. Next, at block 330, the processor 202 determines a time-versus-temperature profile in the interior cavity 111 of the receptacle 110. Then, at block 335, the processor 202 determines that the time-versus-temperature profile in the interior cavity 111 of the receptacle 110 has met preset criteria. And, in response to the time-versus-temperature profile in the interior cavity 111 of the receptacle 110 meeting preset criteria, the processor 202 determines a suspension time for a dehydration cycle, at block 340.

In one optional implementation, the peak temperature ranges from 175° F. to 185° F.

In one optional implementation, continuously monitoring the temperature in the interior cavity 111 of the receptacle 110 includes (i) monitoring at least one temperature sensor 129 coupled to at least one of the bottom support 115 or the cylindrical sidewall 125, (ii) monitoring at least one temperature sensor coupled to the inlet opening 112, (iii) monitoring at least one temperature sensor coupled to the outlet opening 113, and (iv) monitoring at least one temperature sensor arranged in an operating environment 100 of the apparatus 105 external to the receptacle 110.

In one optional implementation, method 300 includes the processor 202 reducing the heat in the interior cavity 111 of the receptacle 110 to a range from 135° F. to 145° F. during a cooldown period. In this implementation, the third plurality and the fourth plurality of paddles 165, 175 continue to rotate and thereby further break down the food waste.

In one optional implementation, the top edge 151, 161 of each of the first and the second plurality of paddles 145, 155 is serrated. In this implementation, method 300 further includes breaking apart the food waste, via serrations of each of the first and the second plurality of paddles 145, 155, when food waste is received in the receptacle 110.

In one optional implementation, method 300 further includes the processor 202 opening the gate 101 during an unload cycle in response to receiving a signal from a user input device 139. In this implementation, the third plurality and the fourth plurality of paddles 165, 175 rotate for a preset cycle time thereby advancing dehydrated food waste through the first opening 116 in the bottom support 115 of the receptacle 110.

In one optional implementation, method 300 further includes an air blower 192 advancing moist air from the interior cavity 111 of the receptacle 110 into a first conduit 193 of the heat exchanger 191 and through a circular filter 194. The circular filter 194 separates particles from the moist air. The air blower 192 advances the moist air from the circular filter 194 to the second conduit 195. A water-cooled pipe 196 contained in the second conduit 195 separates water from the moist air, thereby dehumidifying the moist air. A drainage pipe drains 197 the separated water from the second conduit 195. The air blower 192 advances the dehumidified air to a third conduit 198 that includes a heating element 199 arranged therein. The heating element 199 heats the dehumidified air. And the air blower 192 advances the heated dehumidified air into the interior cavity 111 of the receptacle 110. In one optional implementation, the heated dehumidified air has a temperature ranging from 165° F. to 225° F.

In one optional implementation, receiving the food waste in the interior cavity 111 of the receptacle 110 includes (i) partially loading the interior cavity 111 of the receptacle 110, (ii) rotating, via the shaft 135, the third plurality and the fourth plurality of paddles 165, 175 until the food waste breaks apart and reduces in height within the receptacle 110, and (iii) loading additional food waste into the interior cavity 111 of the receptacle 110.

In one optional implementation, method 300 further includes sterilizing the food waste, via at least one UV light 128 arranged in the top support 120 of the receptacle 110, by mixing the food waste and exposing the food waste to UV light.

In one optional implementation, rotating the third plurality and the fourth plurality of paddles 165, 175 and thereby mixing the food waste is conducted on a rotation cycle that includes (i) rotating the third plurality and the fourth plurality of paddles 165, 175 in a forward direction of rotation for 20 minutes, (ii) rotating the third plurality and the fourth plurality of paddles 165, 175 in a rearward direction of rotation for 2 minutes thereby reducing build-up of the food waste on the first, second, third, and fourth plurality of paddles 145, 155, 165, 175, and (iii) repeating, via the processor 202, the rotation cycle until the suspension time for the dehydration cycle is reached.

In one optional implementation, method 300 further includes the processor 202 continuously monitoring a motor amperage of the gear motor 140. The processor 202 determining that the motor amperage reached an amperage threshold. And the processor 202 reduces a speed of the gear motor 140 by half.

In one optional implementation, method 300 further includes the processor 202 determining that the motor amperage is 175% of a full amperage load. And the third plurality and the fourth plurality of paddles 165, 175 rotating in alternating rearward and forward directions thereby releasing a jam between the food waste and at least one of the first, the second, the third, and the fourth plurality of paddles 145, 155, 165, 175.

In one optional implementation, method 300 further includes the processor 202 receiving identifying information for the contents of the food waste. And the processor 202 associating the identifying information with a bar code configured to permit traceability of the dehydrated food waste.

In one optional implementation, method 300 further includes the processor 202 sending the identifying information to at least one data storage 206 that is either remote or local to the apparatus 105.

The description of different advantageous arrangements has been presented for purposes of illustration and description and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

We claim:

1. An apparatus for treating food waste, comprising:
a receptacle having a bottom support, a top support, and a cylindrical sidewall extending therebetween, wherein the receptacle has an interior cavity, wherein the top support has a first opening configured to receive the food waste, and wherein the bottom support has a first opening to release dehydrated food waste;
a load door coupled to the first opening in the top support;
a shaft rotatably arranged concentrically within the interior cavity of the receptacle and extending through a second opening in the bottom support of the receptacle and through a second opening in the top support of the receptacle such that the shaft is oriented vertically;
a gear motor coupled to the shaft via one or more gears, a roller chain, or a drive belt;
a first plurality of paddles each having a first end coupled to a first hub that is disposed concentrically about the shaft in a spaced-apart arrangement, the first plurality of static paddles each having a second end extending radially from the first hub such that the second end is coupled to the cylindrical sidewall of the receptacle;
a second plurality of paddles each having a first end coupled to a second hub that is disposed concentrically about the shaft in a spaced-apart arrangement below the first hub, the second plurality of static paddles each having a second end extending radially from the second hub such that the second end is coupled to the cylindrical sidewall of the receptacle, wherein the first and the second plurality of paddles are configured to be static;
a third plurality of paddles coupled to a third hub that is coupled to the shaft between the first hub and the second hub;
a fourth plurality of paddles coupled to a fourth hub that is coupled to the shaft between the second hub and the bottom surface of the receptacle, wherein the third plurality of paddles and the fourth plurality of paddles are configured to rotate with the shaft;
at least one heat source comprising one or more of (i) at least one heating pad coupled to the bottom support and/or the cylindrical sidewall of the receptacle, (ii) a heat exchanger coupled to the receptacle via an inlet opening and an outlet opening, and (iii) at least one microwave coupled to the top support and configured to emit microwaves into the interior cavity of the receptacle; and
a gate coupled to the bottom support of the receptacle, wherein the gate is configured to move between a closed position such that the gate creates a watertight seal with the first opening in the bottom support of the receptacle and an open position that permits the dehydrated food waste to exit the interior cavity of the receptacle through the first opening in the bottom support.

2. The apparatus of claim 1, wherein the first and the second plurality of paddles each have a front surface and an opposing back surface extending between a top edge and a bottom edge such that the front surface is arranged vertically relative to the bottom support of the receptacle, wherein the top edge of each of the first and the second plurality of paddles is serrated.

3. The apparatus of claim 2, wherein the bottom edge of each of the first and the second plurality of paddles is serrated.

4. The apparatus of claim 2, further comprising a wedge support that is coupled to the back surface of each of the first and the second plurality of paddles.

5. The apparatus according to claim 1, wherein the first plurality of paddles comprises three paddles arranged 120 degrees apart about the first hub, wherein the second plurality of paddles comprises three paddles arranged 120 degrees apart about the second hub, and wherein the first plurality of paddles and the second plurality of paddles are offset from each other by 60 degrees.

6. The apparatus of claim 1, wherein the third plurality of paddles each comprise (i) a front surface and an opposing back surface extending between a top edge and a bottom edge such that the front surface is arranged vertically relative to the bottom support of the receptacle and (ii) a support arm coupled to the front surface, wherein the support arm has a beveled front edge, wherein the third plurality of paddles each have an inner segment and an outer segment, wherein the outer segment is arranged at a forward angle relative to the inner segment such that each of the third plurality of paddles is curved and thereby configured to move the food waste toward the shaft when the third plurality of paddles is moving in a forward direction of rotation.

7. The apparatus of claim 6, wherein the top edge of each of the third plurality of paddles has a beveled angle and/or is serrated.

8. The apparatus according to claim 6, wherein the bottom edge of each of the third plurality of paddles has a beveled angle and/or is serrated.

9. The apparatus according to claim 6, wherein the third plurality of paddles comprises two paddles arranged on opposing sides of the third hub.

10. The apparatus of claim 1, wherein the fourth plurality of paddles each comprise (i) an inner paddle portion and an outer paddle portion each having a front surface and an opposing back surface extending between a top edge and a bottom edge, wherein the front surface of each of the fourth plurality of paddles is angled toward the top surface of the receptacle and the bottom edge is arranged as a leading edge and the top edge is arranged as a trailing edge in a forward direction of rotation, (ii) a support arm having an inner segment and an outer segment, wherein the inner segment of the support arm is coupled to the back surface of the inner paddle portion and the outer segment of the support arm is coupled to the back surface of the outer paddle portion, wherein the outer segment is arranged at a lag angle relative to the inner segment such that each of the fourth plurality of paddles is curved such that the inner paddle portion is configured to advance the food waste forward and the outer paddle portion is configured to advance the food waste toward and/or upward along the cylindrical sidewall of the receptacle.

11. The apparatus of claim 10, wherein the top edge of each of the inner paddle portions and the outer paddle portions of the fourth plurality of paddles has a beveled angle and/or is serrated.

12. The apparatus according to claim 10, wherein the third plurality of paddles comprises two paddles arranged on opposing sides of the third hub, wherein the fourth plurality of paddles comprises two paddles arranged on opposing sides of the fourth hub, wherein the third plurality of paddles and the fourth plurality of paddles are offset from each other by 90 degrees.

13. The apparatus of claim 1, wherein the at least one heat source comprises a first heating pad coupled to an exterior of the bottom support of the receptacle and a second heating pad coupled to an exterior of the cylindrical sidewall at a location between the bottom support and a midpoint along a height of the cylindrical sidewall.

14. The apparatus of claim 1, wherein the at least one heat source comprises a plurality of heating pads coupled to an exterior of the bottom support of the receptacle and a heating pad coupled to an exterior of the cylindrical sidewall adjacent to the bottom support.

15. The apparatus of claim 1, wherein the at least one heat source comprises three heating pads coupled to the exterior of the bottom support and a heating pad coupled to the exterior of the cylindrical sidewall adjacent to the bottom support, wherein the three heating pads are each arranged to cover a substantial portion of a quadrant of the circular bottom support, wherein the three heating pads are further arranged to accommodate the gate that is arranged in a fourth quadrant underneath the opening in the bottom support and to accommodate the shaft and a drive mechanism.

16. The apparatus of claim 1, wherein the heat exchanger comprises:
   an air blower that is coupled to the outlet opening via a first conduit that is configured to receive moist air from the interior cavity of the receptacle, the air blower comprises a circular filter configured to separate particles from the moist air;
   a second conduit that is coupled to the air blower and is configured to separate water from the moist air via a water-cooled pipe contained therein;
   a drainage pipe that is coupled to the second conduit and that is configured to receive the water that is separated from the moist air; and
   a third conduit that is coupled to the second conduit and that is arranged to return air to the interior cavity of the receptacle via the inlet opening, the third conduit includes a heating element arranged therein that is configured to heat returning air.

17. The apparatus of claim 16, wherein the heating element is configured to heat the returning air to a temperature ranging from 165° F. to 225° F.

18. The apparatus of claim 1, wherein the at least one heat source comprises at least two microwaves coupled to the top support on opposing sides of the shaft.

19. The apparatus of claim 1, wherein the gate comprises:
   a first metal plate having a first semicircular opening;
   a first Teflon plate having a second semicircular opening, a top surface of the first Teflon plate coupled to a bottom surface of the first metal plate such that the first semicircular opening is aligned with the second semicircular opening;
   a spring washer having an arc shape corresponding to a perimeter of the semicircular opening in the first Teflon plate, the spring washer having a top surface coupled to a bottom surface of the first Teflon plate;
   a stainless steel plate having a semicircular shape and having a top surface slidably coupled to a bottom surface of the spring washer and to the bottom surface of the first Teflon plate;
   a second Teflon plate having a third semicircular opening, a bottom surface of the stainless steel plate slidably coupled to a top surface of the second Teflon plate;
   a second metal plate having a fourth semicircular opening, a top surface of the second metal plate coupled to a bottom surface of the second Teflon plate, wherein the first, the second, the third, and the fourth semicircular openings are aligned with each other, wherein, in the closed position, the stainless steel plate is arranged beneath the first opening in the bottom support of the receptacle and the first and second semicircular openings and above the third and fourth semicircular openings; and
   at least one electric actuator coupled to the stainless-steel plate and configured to move the stainless steel plate between the closed position and the open position, wherein the stainless steel plate is retracted out of alignment with the first opening in the bottom support of the receptacle, the first, the second, the third, and the fourth semicircular openings in the open position.

20. The apparatus of claim 19, further comprising at least one sensor coupled to at least one of the bottom support and the gate, the at least one sensor configured to determine whether the gate is in the closed position or the open position.

21. The apparatus of claim 1, wherein the gear motor is configured to operate in a forward mode and in a reverse mode.

22. The apparatus of claim 1 further comprising:
   at least one UV light source coupled to the top support and configured to emit UV wavelengths into the interior cavity of the receptacle.

23. The apparatus of claim 22 further comprising:
   a processor electrically coupled to the gear motor, the at least one heat source, the gate, and the plurality of temperature sensors.

24. The apparatus of claim 23, further comprising a display and at least one user input device electrically coupled to the processor.

25. The apparatus of claim 1 further comprising: a plurality of temperature sensors configured to measure the temperature at the bottom of the receptacle, to measure ambient air temperature in an operating environment of the apparatus external to the receptacle, and to measure the temperature of the air at the outlet opening and at the inlet opening.

26. The apparatus of claim 1, wherein the load door comprises a microwave choke and a metallic finger-stock gasket configured to create a seal against microwaves, and wherein the load door comprises a silicon gasket.

27. The apparatus of claim 1, further comprising:
   a load chute coupled to the opening and to the load door, the load chute disposed at a 20° angle; and
   an external housing enclosing the load chute, the receptacle, the at least one heat source, the gear motor, and the gate.

28. A method for operating the apparatus of claim 1, the method comprising:
   receiving the food waste in the interior cavity of the receptacle;
   continuously monitoring, via a processor, a temperature in the interior cavity of the receptacle;
   rotating, via the shaft, the third plurality and the fourth plurality of paddles and thereby mixing the food waste;
   heating, via the at least one heat source, the food waste to a peak temperature;
   determining, via the processor, that the temperature in the interior cavity of the receptacle has reached the peak temperature;
   determining, via the processor, a time-versus-temperature profile in the interior cavity of the receptacle;
   determining, via the processor, that the time-versus-temperature profile in the interior cavity of the receptacle has met preset criteria; and in response to the time-versus-temperature profile in the interior cavity of the receptacle meeting preset criteria, determining, via the processor, a suspension time for a dehydration cycle.

29. The method of claim 28, wherein the peak temperature ranges from 175° F. to 185° F.

30. The method of claim 28, wherein continuously monitoring the temperature in the interior cavity of the receptacle comprises:

monitoring at least one temperature sensor coupled to at least one of the bottom support or the cylindrical sidewall;

monitoring at least one temperature sensor coupled to the inlet opening;

monitoring at least one temperature sensor coupled to the outlet opening; and monitoring at least one temperature sensor arranged in an operating environment of the apparatus external to the receptacle.

31. The method of claim 28, further comprising:

reducing, via the processor, the heat in the interior cavity of the receptacle to a range from 135° F. to 145° F. during a cooldown period; and continuing to rotate the third plurality and the fourth plurality of paddles and thereby further breaking down the food waste.

32. The method of claim 28, wherein the top edge of each of the first and the second plurality of paddles is serrated, the method further comprising:

breaking apart the food waste, via serrations of each of the first and the second plurality of paddles, when food waste is received in the receptacle.

33. The method of claim 28, further comprising:

opening the gate, via the processor, during an unload cycle in response to receiving a signal from a user input device;

rotating the third plurality and the fourth plurality of paddles for a preset cycle time thereby advancing dehydrated food waste through the first opening in the bottom support of the receptacle.

34. The method of claim 33, further comprising:

receiving, via the processor, identifying information for the contents of the food waste; and associating, via the processor, the identifying information with a bar code configured to permit traceability of the dehydrated food waste.

35. The method of claim 28, further comprising:

advancing, via an air blower, moist air from the interior cavity of the receptacle into a first conduit of the heat exchanger and through a circular filter;

separating particles from the moist air, via the circular filter;

advancing, via the air blower, the moist air from the circular filter to the second conduit;

separating water from the moist air, via a water-cooled pipe contained in the second conduit, thereby dehumidifying the moist air;

draining the separated water from the second conduit, via a drainage pipe;

advancing, via the air blower, the dehumidified air to a third conduit that includes a heating element arranged therein;

heating the dehumidified air via the heating element; and advancing, via the air blower, the heated dehumidified air into the interior cavity of the receptacle.

36. The method of claim 35, wherein the heated dehumidified air has a temperature ranging from 165° F. to 225° F.

37. The method of claim 28, wherein receiving the food waste in the interior cavity of the receptacle comprises:

partially loading the interior cavity of the receptacle;

rotating, via the shaft, the third plurality and the fourth plurality of paddles until the food waste breaks apart and reduces in height within the receptacle; and loading additional food waste into the interior cavity of the receptacle.

38. The method of claim 28, further comprising:

sterilizing the food waste, via at least one UV light arranged in the top support of the receptacle, by mixing the food waste and exposing the food waste to UV light.

39. The method of claim 28, wherein rotating the third plurality and the fourth plurality of paddles and thereby mixing the food waste is conducted on a rotation cycle comprising:

rotating the third plurality and the fourth plurality of paddles in a forward direction of rotation for 20 minutes;

rotating the third plurality and the fourth plurality of paddles in a rearward direction of rotation for 2 minutes thereby reducing build-up of the food waste on the first, second, third, and fourth plurality of paddles; and repeating, via the processor, the rotation cycle until the suspension time for the dehydration cycle is reached.

40. The method of claim 28, further comprising:

continuously monitoring, via the processor, a motor amperage of the gear motor;

determining, via the processor, that the motor amperage reached an amperage threshold; and reducing, via the processor, a speed of the motor by half.

41. The method of claim 40, further comprising:

determining, via the processor, that the motor amperage is 175% of a full amperage load; and rotating the third plurality and the fourth plurality of paddles in alternating rearward and forward directions thereby releasing a jam between the food waste and at least one of the first, the second, the third, and the fourth plurality of paddles.

42. The method of claim 28, further comprising:

sending, via the processor, the identifying information to at least one data storage that is either remote or local to the apparatus.

* * * * *